US008551722B2

(12) United States Patent
LM Hemker et al.

(10) Patent No.: US 8,551,722 B2
(45) Date of Patent: Oct. 8, 2013

(54) TIME-COURSE MEASUREMENT OF ENZYMATIC ACTIVITY CORRECTED FOR IMPACTS OF DISTURBANCES RELATING TO THE REACTION OF THE ENZYME WITH A SUBSTRATE

(75) Inventors: Hendrik Coenraad LM Hemker, Maastricht (NL); Pieter Wilhelm Hemker, AL Amsterdam (NL)

(73) Assignee: Synapse B.V., Maastricht (NL)

( * ) Notice: Subject to any disclaimer, the term of this patent is extended or adjusted under 35 U.S.C. 154(b) by 142 days.

(21) Appl. No.: 12/866,777

(22) PCT Filed: Feb. 6, 2009

(86) PCT No.: PCT/EP2009/051413
§ 371 (c)(1),
(2), (4) Date: Sep. 22, 2010

(87) PCT Pub. No.: WO2009/098313
PCT Pub. Date: Aug. 13, 2009

(65) Prior Publication Data
US 2011/0045512 A1    Feb. 24, 2011

(30) Foreign Application Priority Data

Feb. 7, 2008  (EP) .................................... 08151181

(51) Int. Cl.
*C12Q 1/56*  (2006.01)
(52) U.S. Cl.
USPC .......................................................... 435/13
(58) Field of Classification Search
USPC .......................................... 435/13; 530/802
See application file for complete search history.

(56) References Cited

U.S. PATENT DOCUMENTS

| 4,287,180 A * | 9/1981 | Thomas ..................... 424/94.64 |
| 2006/0051828 A1 * | 3/2006 | Giesen et al. .................... 435/13 |
| 2010/0105091 A1 * | 4/2010 | Giesen et al. .................... 435/13 |

FOREIGN PATENT DOCUMENTS

| WO | 03093831 A1 | 11/2003 |
| WO | 2007141023 A2 | 12/2007 |

OTHER PUBLICATIONS

Gerotziafas G. et al. Towards a Standardization of Thrombin Generation Assessment. Thrombosis J 3(16)1-11, Oct. 2005.*
DeSmedt E. et al. The Technique of Measuring Thrombin Generation with Fluroogenic Substrates. Thrombosis Haemostasis 100(2)343-349, Aug. 2008.*
Goudar C. et al. Progress Curve Analysis for Enzyme and Microbial Kinetic Reactions . . . . J of Microbiological Methods 59:317-326, 2004.*
Freyburger G. et al: "Generation de thrombine colibree et outomatisee (CAT) : interet d'un troifement du signal par un logiciel developpe sur Excel", Communication Libres: Song Thrombose Volssorux 2008, pp. 47-50.

Giesen, P., "A calibrated automated tool to assess the thrombotic-haemostatic system", Blood Coagulation, May 2005.
Hemker et al., "Phenotyping the Clotting System", Thromb Haemost 2000, vol. 84, pp. 747-751.
Peyrou et al., "Contribution of Erythrocytes to Thrombin Generation in Whole Blood", Thromb Haemost 1999, vol. 81, pp. 400-406.
Giesen et al., "Blood-borne Tissue Factor: Another View of Thrombosis", Proc. Natl. Acad. Sci. USA, Mar. 1999, Medical Sciences, vol. 96, pp. 2311-2315.
Hemker, H. Coenraad, "Platelet Procoagulant Activities: the Amplification Loops Between Platelets and the Plasmatic Clotting System", Platelets in Thrombotic and non-Thrombotic Disorders, 2002, pp. 381-392.
Beguin et al., "Thrombin, Fibrin and Platelets: a Resonance Loop in which von Willebrand Factor is a Necessary Link", Thrombosis and Haemostasis, 1997, vol. 78, No. 1, pp. 590-594.
Beguin et al., "Fibrin-Dependent Platelet Procoagulant Activity Requires GPIb Receptors and von Willebrand Factor", Blood, Jan. 15, 1999, vol. 93, No. 2, pp. 564-570.
"Prevention of Pulmonary Embolism and Deep Vein Thrombosis with Low Dose Aspirin: Pulmonary Embolism Prevention (PEP) Trial", Pulmonary Embolism Prevention (PEP) Trial Collaborative Group, Lancet 2000, vol. 355, pp. 1295-1302.
Nicolaes et al., "Effect of Activated Protein C on Thrombin Generation and on the Thrombin Potential in Plasma of Normal and APC-Resistant Individuals", Blood Coagulation and Fibrinolysis, 1996, vol. 8, pp. 28-38.
Rosing et al., "Oral Contraceptives and Venous Thrombosis: Different Sensitivities to Activated Protein C in Women Using Second- and Third-Generation Oral Contraceptives", British Journal of Haematology, Rapid Paper, 1997, vol. 97, pp. 233-238.
Regnault et al., "Thrombinography Shows Acquired Resistance to Activated Protein C in Patients with Lupus Anticoagulants", Thromb Haemost 2003, vol. 89, pp. 208-212.

(Continued)

*Primary Examiner* — Ralph Gitomer
(74) *Attorney, Agent, or Firm* — Young & Thompson

(57) ABSTRACT

A method of determining the course of enzyme activity that is variable in time, wherein the activity is probed by conversion of a substrate of the enzyme, includes, in a selected test set up and for a determined substrate of the enzyme, determining the velocity of signal production ($dF_{diag}/dt$) resulting from a time curve of the signal ($F_{diao}=f(A)$) obtained from splitting the substrate when it is contacted with a determined initially fixed concentration of the enzyme (E) and providing a "diagnostic plot" with the values of ($dF_{diag}/dt$) against the signal ($F_{diag}$) and determining whether the diagnostic plot is either a straight line or a parabola and in the same test conditions, for a given test sample, determining the signal production ($F_{exp}$) resulting from splitting the substrate by the enzyme generating in and/or disappearing from the sample and providing the time curve of signal $F_{exp}=f(t)$; and transforming the obtained experimental value of the signal ($F_{exp}$) into an ideal value ($F_{transf}$).

28 Claims, 14 Drawing Sheets

(56) References Cited

OTHER PUBLICATIONS

Figure 1:
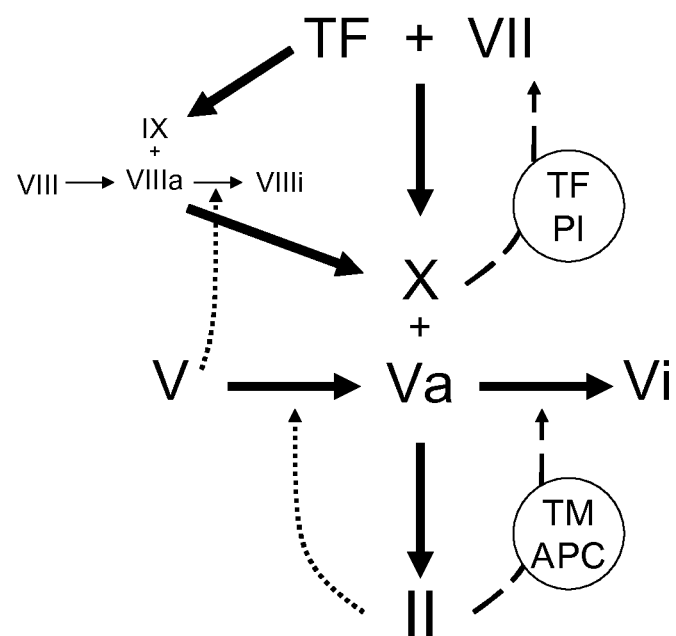

Tanis et al., "Procoagulant Factors and the Risk of Myocardial Infarction in Young Women", European Journal of Haematology, 2006, vol. 77, pp. 67-73.

Redondo et al., "Coagulation Factors II, V, VII, and X, Prothrombin Gene 20210G A Transition, and Factor V Leiden in Coronary Artery Disease", Arterioscler Thromb Vasc Biol., 1999, vol. 19, pp. 1020-1025.

Faber et al., "Thrombin Generation in Platelet-Rich Plasma as a Tool for the Detection of Hypercoagulability in Young Stroke Patients", Pathophysiol Haemost Thromb, 2003, vol. 33, pp. 52-58.

Dargaud et al., "Evaluation of Thrombin Generating Capacity in Plasma from Patients with Haemophilia A and B", Thromb Haesmost, 2005, vol. 93, pp. 475-480.

Siegemund et al., "Thrombin Generation in Severe Haemophilia A and B: the Endogenous Thrombin Potential in Platelet-rich Plasma", Thromb Haemost, 2003, vol. 90, pp. 781-786.

Keularts et al., "The Role of Factor XI in Thrombin Generation Induced by Low Concentrations of Tissue Factor", Thromb Haemost, 2001, vol. 85, pp. 1060-1065.

Al Dier et al., "The Thrombogram in Rare Inherited Coagulation Disorders: Its Relation to Clinical Bleeding", Thromb Haemost, 2002, vol. 88, pp. 576-582.

Keularts et al., "The Effect of DDAVP Infusion on Thrombin Generation in Platelet-rich Plasma of von Willebrand Type 1 and in Mild Haemophilia A Patients", Thromb Haemost, 2000, vol. 84, pp. 638-642.

Dargaud et al., "Major Surgery in a Severe Haemophilia A Patient with High Titre Inhibitor: Use of the Thrombin Generation Test in the Therapeutic Decision", Haemohilia, Case Report, 2005, vol. 11, pp. 552-558.

Dargaud et al., "A Case of Glanzmann's Thrombasthenia Successfully Treated with Recombinant Factor Viia During a Surgical Procedure: Observations on the Monitoring and the Mechanism of Action of This Drug", Haematologica, 2006, vol. 91, No. 4, pp. e-58-e61.

Hemker et al., "Thrombin Generation Assays: Accruing Clinical Relevance", Current Opinion in Hematology, 2004, vol. 11, pp. 170-175.

Hemker et al., "Calibrated Automated Thrombin Generation Measurement in Clotting Plasma", Pathophysiol Haemost Thromb, 2003, vol. 33, pp. 4-15.

Varadi et al., "Thrombin Generation Assay and Other Universal Tests for Monitoring Haemophilia Therapy", Haemophilia, 2004, vol. 10, Suppl. 2, pp. 17-21.

Hemker et al., "The Thrombogram: Monitoring Thrombin Generation in Platelet Rich Plasma", Thromb Haemost, 2000, vol. 83, pp. 589-591.

Hemker et al., "Thrombin Generation in Plasma: Its Assessment Via the Endogenous Thrombin Potential", Thrombosis and Haemostasis, 1995, vol. 74, No. 1, pp. 134-138.

Meyer et al., "One-Point Recalibration of Heterogeneous Enzyme Immunoassays with Non-Linear Calibration Curves", Clinical Chemistry, 1988, vol. 34, No. 1, pp. 113-117.

Heller et al., "Fluorimetric Studies on Epinephrine and I-Arterenol in Plasma", The American Journal of Physiology, 1951, vol. 166, pp. 304-313.

Silva et al., "Direct Determination of Propranolol in Urine by Spectrofluorimetry with the Aid of Second Order Advantage", Analytica Chimica Acta, 2007, vol. 595, pp. 282-288.

Palmier et al., "Rapid Determination of Enzyme Kinetics from Fluorescence: Overcoming the Inner Filter Effect", Analytical Biochemistry, 2007, vol. 371, pp. 43-51.

Goudar et al., "Progress Curve Analysis for Enzyme and Microbial Kinetic Reactions Using Explicit Solutions Based on the Lambert W Function", Journal of Microbiological Methods, 2004, vol. 59, pp. 317-326.

Holzhutter et al., "A New Method of Parameter Estimation from Progress Curves", Biomed. Biochim. Acta, 1984, vol. 43, No. 6, pp. 813-820.

Kuttner et al., "The Use of Progress Curves for the Estimation of Inactivation Rate Constants of Enzymes", 1985, vol. 44, No. 7/8, pp. 1025-1034.

Hemker et al., "Caution in the Interpretation of Continuous Thrombin Generation Assays: a rebuttal", Journal Thromb Haemost, letters to the Editor, 2007, vol. 5, pp. 1085-1087.

Hemker et al., "Continuous Registration of Thrombin Generation in Plasma, Its Use for the Determination of the Thrombin Potential", Thrombosis and Haemostasis, 1993, vol. 70, No. 4, pp. 617-624.

Ramjee, Manoj K., "The Use of Fluorogenic Substrates to Monitor Thrombin Generation for the Analysis of Plasma and Whole Blood Coagulation", Analytical Biochemistry, 2000, vol. 277, pp. 11-18.

Hendrix et al., "Activation of Human Prothrombin by Stoichiometric Levels of Staphylocoagulase", The Journal of Biological Chemistry, 1983, vol. 258, No. 6, pp. 3637-3644.

\* cited by examiner

TIME-COURSE MEASUREMENT OF ENZYMATIC ACTIVITY CORRECTED FOR IMPACTS OF DISTURBANCES RELATING TO THE REACTION OF THE ENZYME WITH A SUBSTRATE

This application is a National Stage application filed under Rule 371 based on PCT/EP09/51413 filed Feb. 6, 2009, which is based on EP 08151181.8 filed Feb. 7, 2008.

The invention relates to time-course measurement of enzymatic activity corrected for impacts of disturbances relating to the reaction of the enzyme with a substrate.

The in vitro method of the invention is especially carried out in the field of blood tests and in particular it is intended for the measurement of clotting or the fibrinolysis activity in vitro.

The invention thus proposes a method to measure the exact time course of an enzymatic activity that develops and/or disappears in a reaction mixture, especially in a blood sample.

According to a particular aspect of the invention, the method of the invention is performed in order to measure or to monitor the development of thrombin and/or plasmin in a sample previously obtained from a patient tested for a possible thrombotic or bleeding disease and/or under drug prescription, wherein said drug may interact with the coagulation or with the fibrinolysis process in vivo.

Thrombotic diseases, such as coronary infarction, stroke, pulmonary embolism and several others are responsible for about half of all death and disability in western society. In developing countries they increase with the degree of development. Bleeding disease, although numerically less important, are also a significant cause of death. Thus over- or under-function of the haemostatic system is an extremely important pathogenetic mechanism. It therefore is all the more surprising that a good clinical function test is not available.

The Role of Thrombin in Haemostatic and Thrombotic Disease:

In haemostasis and thrombosis thrombin plays a pivotal role. In venous thrombotic disease this has long since been recognized and is convincingly demonstrated by the fact that prevention and treatment of venous thrombosis is best brought about by decreasing thrombin activity, either by direct inhibition (hirudin, melagatran) or by decreased synthesis (vitamin K antagonists) or by increased decay (heparins). In the last decennia it became increasingly clear that thrombin is as important in arterial disease as it is in venous disease. Clinical trials have shown that vitamin K antagonists as well as heparin decrease the reoccurrence rate of the arterial disease myocardial infarction. A role for thrombin in bleeding is suggested by the bleeding tendency that develops when thrombin generation is as profoundly affected as in severe overdosage of oral anticoagulants or heparin. Also the haemophilias are diseases of the thrombin forming system. For an extensive review of these matters see [1]

All Elements of the Blood Participate in Thrombin Formation:

Modern research has led to the recognition that thrombin is formed through the cooperation of the formed elements of the blood and plasma. Red blood cells (RBCs) are the least active in this respect although in a small percentage of them the outer membrane exhibits procoagulant activity [2]. Much more important is that white blood cells carry tissue factor activity. This activity normally is concealed but in lesion becomes manifest through interactions with blood platelets [3]. The main players are undoubtedly the platelets and the plasmatic clotting system. In textbooks it is still found that platelets are responsible for primary haemostasis and arterial thrombosis, whereas the clotting of plasma serves for consolidation of the haemostatic plug and is the mechanism behind venous thrombosis. This view is due to the fact that plasma and platelets were studied apart from each other. In reality the cooperation between platelets and plasma and the other cells of the blood is essential in both primary and secondary haemostasis and in arterial and venous thrombosis. Platelet plug formation plays a role in thrombin generation because the interstices in a platelet aggregate form an unstirred niche in which thrombin can form without being swept away by flowing blood. That is why measuring thrombin generation in clotting whole blood is so close to physiological reality.

Apart from forming a "sponge" in which thrombin can form, platelets also actively contribute to the generation of thrombin. They shed factor V and provide the procoagulant phospholipid surface required for prothrombin conversion as well as for the different steps in the coagulation mechanism that lead to prothrombinase formation ([4]). The velocity of thrombin generation and the amount formed thus depends upon platelet activity as well as on the plasma proteins involved. Particularly interesting is the role of polymerizing fibrin. Von Willebrand factor (vWf) interacts with polymerizing fibrin and undergoes a conformational change which makes it reactive to platelet receptor GPIb and through this binding cooperates to the platelet becoming procoagulant [5,6]. This shows that forming a fibrin clot is not the closing act of haemostasis and that thrombin formation in a plug (or thrombus, or clot) is a key event in the process. Indeed, as we will see below, >95% of all the thrombin formed is formed after clotting has taken place and this thrombin is essential in the haemostasis and thrombosis process. Perhaps the best proof of the tight bonds between platelets and the plasmatic clotting system is the fact that all "aggregation inhibitors" and other antiplatelet agents also inhibit thrombin generation in platelet rich plasma (or whole blood). This has been shown for aspirin, abciximab, MK383 and clopidogrel (see [1] for a review). Inversely, the fact that the antiplatelet drug par excellence, aspirin, prevents venous thrombosis [7] further illustrates the close connection between platelet function and blood coagulation.

So, in summary, the amount of thrombin formed in a clot is an essential feature in the process of haemostasis and thrombosis and all the elements of blood take part in its formation.

Thrombin Generation (TG) as an Indicator of Thrombotic- and Bleeding Risk:

Increased TG invariably indicates thrombotic risk, whether it is due to deficiency of antithrombin or an excess of prothrombin. Also in disorders in the protein C pathway (deficiency of proteins S and C, factor $V_{Leiden}$) that are known to cause a thrombotic tendency, thrombin generation is higher than normal. This holds for plasma clotting as such, but becomes especially obvious if the protein C pathway is activated by thrombomodulin (TM) (FIG. 1). The thrombotic tendency induced by oral contraceptives can be attributed to an acquired resistance to activated protein C that causes a 10% increase of thrombin generation which becomes more obvious when TM or APC is added [8,9].

A particularly interesting case is the lupus anticoagulant. This type of auto-antibody induces an increase of the lag time of thrombin formation, and therefore an increase of clotting time, but also an important resistance to the activity of the protein C system [10] and hence increase of thrombin generation. This explains the "LAC paradox" i.e. an anticoagulant effect that is accompanied by a thrombotic tendency.

Excess amounts of factors II, V,[11] VIII and IX have been found to correlate with the occurrence of myocardial infarction [12]. Also higher than normal levels of vWF increase thrombin generation and are a risk factor for arterial thrombosis [11].

In a sub-population of young stroke patients (around 30%) both thrombin generation in Platelet Rich Plasma (PRP) and vWF have been shown to be significantly higher than normal [13]. In all congenital coagulation factor deficiencies thrombin generation is decreased. This has been demonstrated for the haemophilias A, B and C (deficiency of factor VIII, IX or XI; [14-16] as well as for all rare clotting factor deficiencies (prothrombin, factors V, VII, X, XII;)[17]. A bleeding tendency is seen as soon as TG is below 20% of normal. In haemophilia A not only infusion of factor VIII or administration of DDAVP augments the capacity of blood to form thrombin but also inhibitor bypassing therapy with products containing prothrombin and/or factor VII increases thrombin generation [18-20].

Severe thrombopenia (<50000 platelets per μL) causes decreased thrombin generation as well as the Glanzman and Bernard-Soulier thrombopathies. In von Willebrand's disease—hitherto known to induce a disorder of platelet adhesion at high shear rates—thrombin generation in PRP is significantly impaired (see above). Provided that a certain shear stress is induced (stirring) the defect in PRP is much higher than in Platelet Poor Plasma (PPP), which indicates that under these conditions it cannot be explained by the concomitant—usually mild—decrease of factor VIII alone.[6]

The Thrombogram

The following remarks should be taken into consideration with respect to the mechanism of thrombin generation when addressing the problem to be solved according to the invention.

FIG. 1 gives a simplified scheme of the mechanism of thrombin formation. Drawn arrows means conversion into; dotted arrows indicate feedback activations; dashed arrows: feedback inhibition. This scheme shows only the major interactions but it will be clear that the thrombin generating mechanism is extremely complex and replete with positive and negative feedback reactions. Indeed it is so complex as to become a non-linear system, i.e., there are no simple relations between the concentration of the reactants and the outcome and threshold phenomena may cause the system to react essentially unpredictably. In addition the reaction scheme is dependent upon the reaction conditions (e.g. activity of the trigger, i.e. tissue factor) and it is not always known precisely which reactions are in action. The reaction of the whole to a given trigger can therefore not be predicted, even if the individual concentrations of the reactants are known. Only a test that measures the function of the complete system as contained in the blood of a patient reveals the haemostatic/thrombotic status of that patient.

Figure 2:
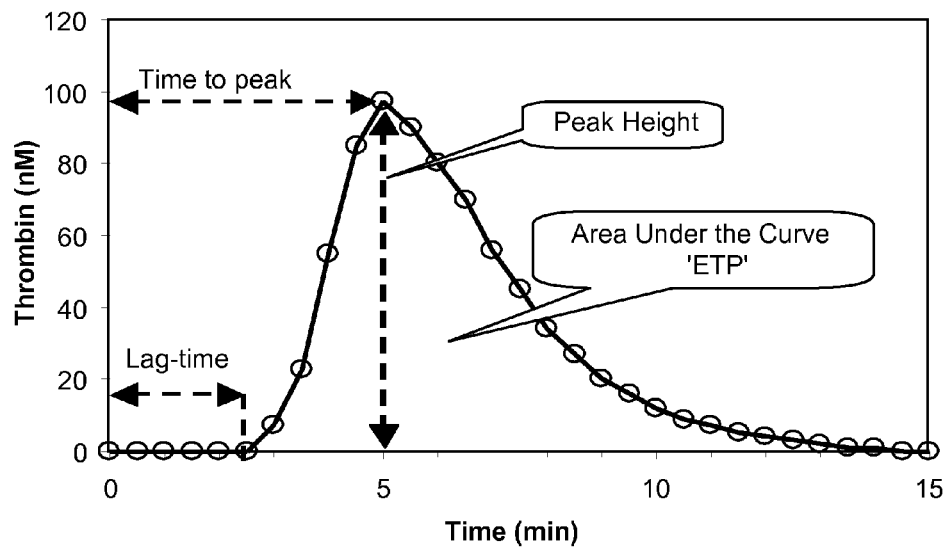

The result of the whole process of thrombin generation is the appearance and disappearance of a transient thrombin activity. The curve of thrombin activity against time, or Thrombogram™ is characterised by an initiation phase, or lag-time, during which only minute amounts of thrombin are formed; then follows a burst of activity, known as the propagation phase (FIG. 2). Blood forms a clot at the very beginning of the burst and almost all thrombin is formed after the clot has formed. All formed thrombin is subsequently inactivated by the antithrombins of the blood. These proteins bind stoichiometrically to thrombin in a slow reaction. The inactivation velocity is proportional to the concentration of thrombin and of antithrombin. As long as the conversion rate of prothrombin is higher than the inactivation rate of thrombin the level of thrombin increases. As the level of thrombin increases the inactivation rate also increases. At the peak both velocities are equal, thereafter decay predominates. The obtained curve of thrombin activity shows the various phases and especially shows the lag time before thrombin generation starts, the peak of thrombin generation, the time to reach the peak and the ETP.

The concept of "enzyme potential" is now defined as the amount of enzymatic work that can potentially be done by an enzyme acting on a substrate. If an enzyme at concentration E acts upon a substrate of concentration S with kinetic constants $k_{cat}$ and Km during a time t, than the amount of substrate converted is $P(t)=tE(t)(k_{cat}S(t)/(Km+S(t)))$. Km and $k_{cat}$ are substrate dependent, E and t are substrate-independent. E multiplied by t (dimension concentration×time (nM.min)) determines the amount of product that potentially can be produced from a given substrate, provided that the substrate is not exhausted. E multiplied by t is therefore called the enzyme potential ($\eta$). It is essential to note that this concept is meant to include the situation that the enzyme concentration changes in time, i.e. E is an unknown function of t (E(t)). This is e.g. the case with enzymes that are generated and subsequently inactivated in a reaction mixture, like thrombin or plasmin in blood. It is equally important to note that $\eta$ is independent of the substrate properties and concentration. A particular case of the enzyme potential is the ETP which is defined as the total area under the thrombin-time curve from the start of formation of free thrombin until its complete disappearance and which therefore is time independent.

It is further observed that the clotting- and the complement-systems of the blood are replete with amidolytic enzymes that appear and disappear after the function of the system is triggered. The digestive enzymes in the gastrointestinal tract show similar behaviour. Measuring the generation and disappearance of these enzymes, such as e.g. the generation of thrombin or plasmin in blood is a method of increasing clinical relevance [21]. It gives insight into the function of the haemostatic system that cannot be obtained in any other way. Given the fact that about half of all people die from disturbances of the clotting (thrombin) or lysing (plasmin) functions of the blood, its importance can hardly be exaggerated. A convenient way of measurement is by adding a suitable substrate before generation of the enzyme (e.g. thrombin or plasmin) is triggered and monitoring a split product via its optical density (OD), its fluorescence or by other means (e.g. electrochemical). The detecting signal increases during the experiment and the course in time of the concentration of the enzyme (E=g(t)) has to be derived from the course of the experimentally obtained detecting signal ($F_{exp}$=f(t)). The problem thus is how to perform the transformation g(t)→f(t).

Because the enzyme activity determines the velocity of substrate conversion and thus the appearance of the signal, it is clear from the beginning that the relation must be of the type E=g(dF(t)/dt). It is well known to the art how to determine the relation between a known amount of enzyme ($E_{cal}$) and the reaction velocity under initial conditions (=the initial rate, $v_{init}$) and then calculate a calibration factor ($Cf_0$) under these initial rate conditions: $Cf_0=E_{cal}/(dF/dt)$. However, $Cf_0$ cannot a priori be assumed to apply over the whole course of the experiment.

This type of experiments as a rule takes between 10 minutes and several hours, so considerable amounts of product can be formed and the initial substrate concentration ($S_0$) consequently can decrease considerably. Concomitantly the reaction velocity per unit amount of enzyme decreases to a greater or a lesser degree and the velocity of signal production (dF/dt) per unit enzyme decreases during the experiment. The calibration factor (Cf), i.e. the value of dF/dt per unit enzyme, increases when more signal is produced and at every level of signal (F) a different Cf applies. The transformation of $F_{exp}=f(t)$ into the course of enzyme concentration: $E=g(t)$ is no longer possible by the simple application of a fixed calibration factor that is determined under the initial conditions.

Moreover, substrate consumption is not the only cause of variability of Cf. Some thrombin substrates e.g. yield inhibitory split products. With fluorogenic substrates the signal is usually not linearly proportional to the concentration of the product due to the so called inner filter effect. Such disturbances add to the effect of substrate consumption and Cf increases even more in the course of the reaction.

Figure 3:
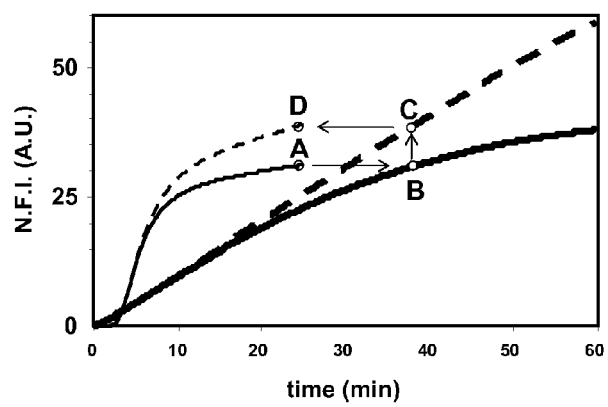

In FIG. 3 the bold black line represents the signal that is obtained when a fixed amount of enzyme is measured under reaction conditions as they are in current use for the measurement of thrombin generation [22]. The bending of this line illustrates how the observed reaction velocity decreases during an experiment although the concentration of enzyme remains constant. This is caused by both substrate consumption and the inner filter effect. The dashed bold line is the straight line that would have been obtained if neither substrate consumption nor inner filter effect would have played a role, i.e. under ideal circumstances. The problem in measuring variable enzymatic activity like a thrombin generation curve, is that an exact calculation of enzyme concentrations can be based on ideal values but not on the observed ones. The problem is essentially that of reading on a non-linear reference curve, more precisely, that of finding the value that would have been obtained on a linear reference curve if it would have the same initial slope as the non-linear curve has.

Accordingly, it is an object of the present invention to provide a method to convert the observed signal values ($F_{obs}$) into the ideal ones ($F_{ideal}$), that may be referred to in order to calculate enzyme concentration. A preliminary condition, however, is to correctly obtain calibration under initial conditions.

In the prior art, calibration methods intended for calibration of the initial conditions of the experiment have been proposed that also apply to the most important application, i.e. fluorimetric determination of the thrombin generation curve.

It is generally known in the art that in fluorometry circumstances that are not directly related to the amount of fluorescent material, such as variations in illumination, variations in quenching by the medium and others are directly perceived as variations in the output signal, so that fluorescence intensity as such does not carry information, unless properly calibrated with either a fixed known amount of the fluorescent molecule or a fixed known amount of enzymatic activity that produces a known amount of fluorescent molecules per unit time.

It is equally well known to the art that care should be taken that calibration is carried out under the same conditions as those in the experiment; notably the variable absorption of light by biological (e.g. plasma) samples.

Calibration against a known amount of thrombin activity has the practical advantage that the increase in fluorescence intensity (dF/dt) is related directly to the concentration of enzyme. This should not distract from the fact that it remains dependent upon correct measurement of fluorophore concentrations and therefore is inadequate when the activity of the calibrator-enzyme is not measured in a medium with the same light-adsorption properties as that in the actual experiment.

In whole blood measurements, light penetrates to only a limited and unknown depth. Therefore the volume in which the measurement is carried out is unknown. It has therefore been proposed to compensate for the individual variations in fluorescent yield by adding a fixed amount of fluorophore to the sample (WO 2006/117246).

The problem remains the variation of the ratio between enzyme concentration and reaction velocity (Cf) during the experiment. In prior art this problem has often been neglected and a fixed initial Cf has been employed during the whole of the experiment [23,24]. This may lead to significant errors, unless it can be demonstrated, as in the case of some chromogenic substrates [25], that a sufficiently small fraction of the substrate is consumed during the reaction.

In the prior art, three solutions have been proposed to solve this problem.

In one type of solution the curvature of the non-linear calibrator curve is not analysed but it is assumed that this curve is identical in all experiments except for a scaling factor of the ordinate (e.g. [26]). This is also the solution proposed for the application to the measurement of thrombin generation by Giesen en Van Asten (International Patent Application WO2007141023). Especially in measurements in plasma, where differences are due to different absorption and quenching properties of excitation and emission light, the scaling factor is conventionally found by adding known amounts of the fluorophore ([27,28]). More generally the concentration of a fluorophore in a quenching medium can be determined by adding a standard also when it has different fluorescent properties than the fluorophore that is to be determined (Hayashi Hidechika, Kamata Kazuya, U.S. Pat. No. 5,792,662). This approach has the drawbacks inherent to the fact that the non-linearity of the reference curve remains undefined; i.e. a mathematical curve has to be fitted to the experimental points but there is no theoretical basis for the choice of the model (as is explicitly stated in Giesen en Van Asten, E.P.A WO2007141023). Nevertheless it is assumed to be identical in all curves except for the scaling factor. This assumption can be proven only by establishing the reference curves for every situation, which amounts to establishing a reference curve for each situation, which would annihilate the advantage of this approach. Alternatively it remains unproven, with the possibility that systematic errors arise under those conditions where the assumption is false. In other words, it is a practical shortcut that probably is applicable within certain limits that cannot be defined.

In a second type of solution, the kinetic parameters of the progress curve are analysed and the correct form of the curve is established from a mathematical model ([29-32]. When the model is known that describes both the inner filter effect and the substrate consumption the curved reference curve can, in principle, be constructed from n+1 data-points, where n is the number of independent parameters in the model. In this approach the form of the reference curve follows from the underlying functional model. Its establishment requires a thorough kinetic analysis of the system and advanced mathematics, involving numerical solutions of (often non-linear) differential equations. It therefore is applicable to fundamental research but less practical for routine analysis.

In a third type of solution in existing art (Hemker et al. (WO 03/093831) observed fluorescence values are converted into ideal values by continuous comparison to a simultaneously measured calibrator curve, obtained by adding a fixed, known amount of enzymatic activity. Calibration with free thrombin added to plasma is impossible because it will be rapidly inactivated by the physiological antithrombins in plasma. Therefore, it has been proposed in the prior art to use the $\alpha_2$-Macroglobulin-thrombin complex ($\alpha_2$M-thrombin) as a standard, i.e., a molecule that contains the active site of thrombin but is not subject to inactivation in plasma.

In FIG. 3 the signal from the calibrator (bold drawn line) and the signal from the cuvette in which thrombin generation takes place (thin drawn line) from a typical experiment are shown. The data are handled in the following way: In the origin, the tangent to the calibration curve is constructed (bold dashed line) and the ideally attained fluorescence ($F_{ideal}$) belonging to every observed fluorescence ($F_{obs}$, point B) is found as the point on the tangent line ($F_{ideal}$, point C) that is attained at the same moment as $F_{obs}$. This results in an array of $F_{obs}$—values with corresponding $F_{ideal}$-values. In order to correct the observed values of a TG experiment so as to obtain the corresponding ideal values, each experimental value (A) is replaced with the corresponding ideal value (D) as found in the abovementioned array. This results in the corrected experimental curve (thin dashed line), i.e. the curve that would have been obtained if the same enzymatic activity would always cause the same dF/dt throughout the experiment. The first derivative of the corrected curve, multiplied by $Cf_0$ expresses the amidolytic activity in nM thrombin. This method requires continuous measurement of the calibrator and the sample and continuous comparison of the two in a step-by-step digital procedure. Both the calibrator- and the TG-data are discontinuous series of values at discrete time points. No value on one curve corresponds directly to a value on the other. The procedure therefore requires an awkward numerical procedure for interpolation between experimental points and to cope with experimental scatter.

The present approach differs from the previous ones and overcomes important weaknesses of each of them. Unlike WO07/141023 it establishes the exact form of the reference plot and within defined limits. Also no underlying functional biochemical model is postulated and consequently there is no need for establishing numerous kinetic parameters and the solving of differential equations. Unlike WO 03/093831 it does not require simultaneous measurement of a calibrator in a parallel experiment. In this regard, the invention provides a method which overcomes at least in part the drawbacks faced in the prior art.

The invention provides a response to the observed problem of the variation, and especially the decrease, in velocity of substrate conversion per unit enzyme activity during the experiments, without requiring continuous comparison to an array of values obtained from a parallel calibration experiment as in (WO 03/093831).

The method proposed in accordance to the invention is independent of the cause(s) of this variation, especially of the decrease, substrate consumption, product inhibition, non-linearity between product concentration and the monitoring signal and others. Its application is restricted however to substrates in concentration ranges that fulfil certain conditions that can be found by applying a so called "diagnostic plot" further disclosed below.

The invention thus provides a method to determine the exact course of an enzymatic activity ($E_{expt}$=g(t)) in a reaction mixture in which this activity appears and disappears in the course of time (enzyme generation curve) without the necessity of simultaneously measuring a calibrator curve, to assume dependence on a scaling factor only or a biochemical model.

The enzymatic activity is detected via the conversion of a substrate and monitoring a signal from the reaction product ($F_{expt}$=f(t)).

Accordingly, the present application concerns a method of determination of the course of an enzyme activity in time, wherein said activity is probed by conversion of a substrate of the enzyme, comprising the steps of:

a) in a selected test setup and for a determined substrate of the enzyme, determining the velocity of signal production ($dF_{diag}/dt$) resulting from a time curve of the signal ($F_{diag}$=f(A)) obtained from splitting said substrate when it is contacted with a determined initially fixed concentration of the enzyme (E) and providing a "diagnostic plot" with the values of ($dF_{diag}/dt$) against the signal ($F_{diag}$) and determining whether said diagnostic plot is either a straight line or a parabola and determining the intercept of this diagnostic plot with the abscissa which is α and the intercept of this diagnostic plot with the ordinate which is $V_{init}$;

b) in the same test conditions, for a given test sample, determining the signal production ($F_{exp}$) resulting from splitting the substrate as in a) by the enzyme generating in and/or disappearing from the sample and providing the time curve of signal $F_{exp}$=f(t);

c) transforming the obtained experimental value of the signal ($F_{exp}$) in step b) into an ideal value ($F_{transf}$) by applying the following transformation:
 (i) If the diagnostic plot is a horizontal line, $F_{transf}$=$F_{exp}$
 (ii) if the diagnostic plot is a straight line, $F_{transf}$=−(α ln (1−$F_{exp}$/α) where α is the intercepts with the abscissa as indicated above.
 (iii) if the diagnostic plot is a parabola, $F_{transf}$=α.arctan h ($F_{exp}$/α) where α is as defined above.

d) determining the enzyme concentration ($E_{exp}$), over the time from the transformed signal values ($F_{transf}$) as $E_{exp}V_{init}.F_{transf}/dt$.

Arctan h is the inverse function of the hyperbolic tangent known from mathematics. In view of the above steps, if the enzymatic activity is constant and the diagnostic plot is a straight line, the F exp obeys the function F exp=α(1−exp(−bt)) (where b is a constant that is found as a by-product of the curve fitting) and when the diagnostic plot is a parabola F exp=α tan h(bt). These functions can conveniently be used to find a by curve fitting to a region where the enzymatic activity is known of be constant.

Figure 4:
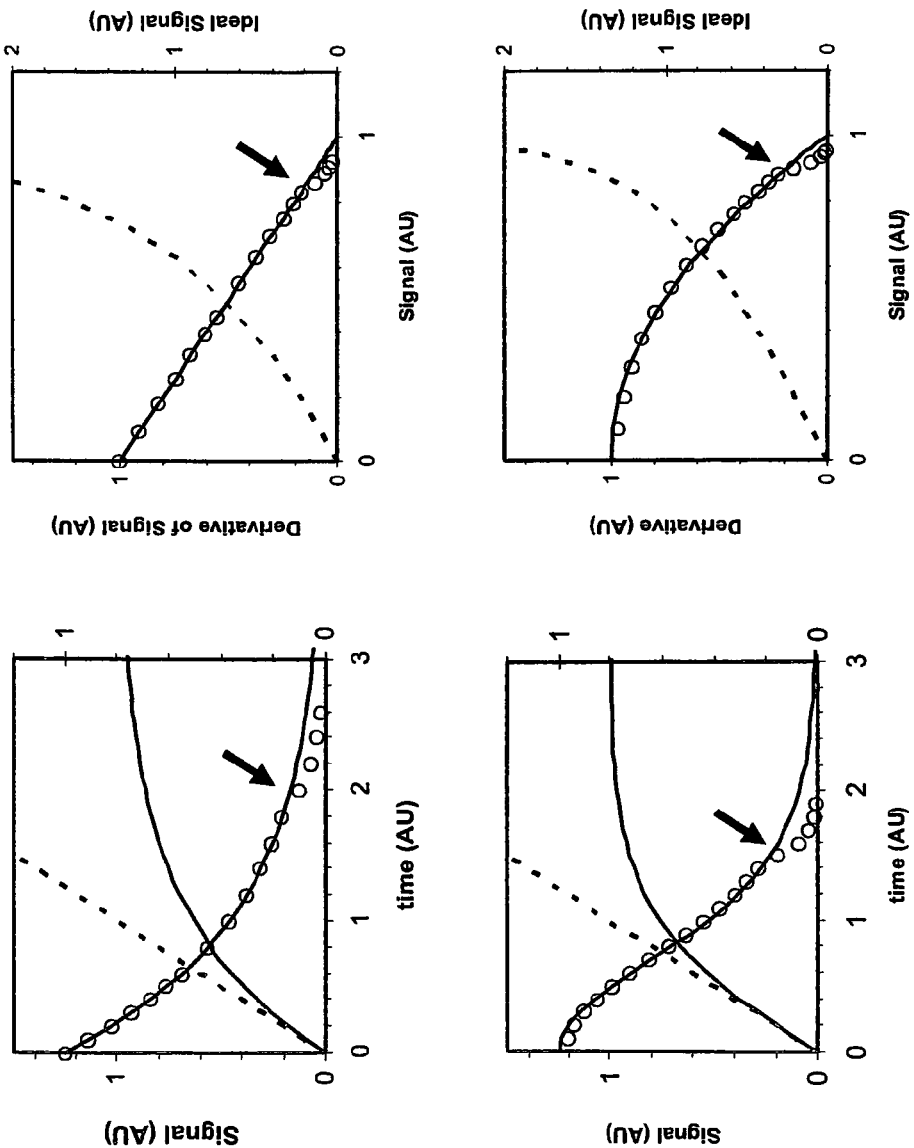

A diagnostic plot is illustrated in FIG. 4.

If and for so far as the diagnostic plot is neither of the above cited plots, the proposed method does not apply.

The invention thus encompasses in a first step, obtaining a diagnostic plot. In order to enable achieving the diagnostic plot, the enzyme concentration and the duration of the experiment should be chosen so that η=t.E covers the enzyme potential to be measured in the generation experiments. In thrombin generation experiments with an enzyme at concentration S and known Km, an ETP of ~(Km+S)/Km μM.min is to be expected so η should be >1.5 this value.

The concentration of substrate is free within a lower limit determined by the possibility to obtain a useful signal and an upper limit of S=3.Km, as higher concentrations disturb the generation mechanism [33].

The measurement of signal (F) at a fixed, known enzyme activity is carried out in the experimental conditions that will apply for the test sample to determine enzyme generation and/or disappearance.

The enzyme activity in time is determined after measuring the signal production in time (velocity of signal production: dFdiag/dt) and preparing a plot of the first derivative of the signal (dFdiag/dt) against the signal (Fdiag) ("diagnostic plot"). In a particular embodiment, the signal is measured until the substrate is exhausted.

The present method applies if the form of the curve compositing the diagnostic plot is either a straight line, i.e., $dF/dt=v_{init}(1-F/\alpha)$ or a parabola, i.e., $dF/dt=v_{init}(1-(F/\alpha)^2)$.

Substrates and substrate concentration ranges that can be profitably used with this method can be defined via the diagnostic plot, if in that plot the enzyme potential, $\eta$=E.t is plotted against the signal F (FIG. 4). If the plot of Df/dt against F is a straight line/parabola until a given value of F ($F_{lim}$) and at $F_{lim}$ the plot of $\eta$ against F indicates an enzyme potential higher than the range to be expected in the generation experiments, than this method can be applied to experiments with that substrate at that concentration, provided that in the range $0-F_{lim}$ a useful experimental signal can be recorded.

$V_{init}$ (initial reaction velocity, at time=0) and $\alpha$ (theoretical upper limit of the signal) are constants that can be obtained directly from the diagnostic plot and are used for the transformation of the data from the enzyme generation experiment into transformed, i.e. corrected signal values ($F_{transf}$) that enable determining the correct enzyme concentration ($E_{exp}$).

There are alternative methods to obtain the constants $v_{init}$ and $\alpha$. $V_{init}$ is the initial rate of substrate conversion and can be found experimentally by any method known to the art. The constant $\alpha$ can be found experimentally by trial and error, because the correct value is the one that transforms into a straight line any experimental curve that is obtained at constant enzyme concentration.

According to a particular embodiment of the invention, the method is carried out to measure an amidolytic enzyme.

According to a particular embodiment, the measurement is performed in a sample which is a blood sample or a plasma sample.

The method of the invention enables to measure the generation of enzyme which gives rise to an increase in enzyme activity and accordingly an increase in substrate consumption and produced signal.

The method of the invention also enables to measure the disappearance of enzyme which gives rise to a decrease in enzyme activity and accordingly a decrease in substrate consumption and produced signal.

In a particular embodiment, the method of determination of the course of an enzyme activity in time is performed with a chromogenic substrate. In such a case, the measurement can be carried out by measuring the optical density of the substrate.

According to another particular embodiment of the invention, the substrate which is used is a fluorogenic substrate. The selection of appropriate substrates for thrombin monitoring may be performed in accordance with the description provided in the examples.

In a particular embodiment, the enzyme, the activity of which is measured is thrombin. In another particular embodiment, the enzyme, the activity of which is measured is plasmin. For both types of enzymes, the measured substrate may be a chromogenic or a fluorogenic substrate.

Fluorogenic substrates may be synthetic substrates, especially for thrombin, coupled with a fluorescent molecule.

In a particular embodiment of the invention, the thrombin substrate is selectively hydrolyzed by thrombin and has a moderate binding affinity for thrombin and a low turnover number.

In another particular embodiment of the invention, the substrate is a fluorogenic substrate and is an oligopeptide having a sequence of two to thirty amino acid residues coupled with a fluorescent molecule.

To illustrate such fluorogenic substrate, oligopeptides having a terminal lysin or arginin for coupling with a fluorescent molecule, may be advantageous.

Particular fluorogenic substrates appropriate for carrying out the invention are Z-Gly-Gly-Arg-AMC, BZ-Phe-Val-Arg-AMC, Z-Gly-Pro-Arg-AMC and Z-Pro-Arg-AMC.

According to another embodiment, the chromogenic substrate suitable to carry out the invention is MSCValArg-pMA or is MZ-Alb-Arg-pNA (SQ68) or DEMZ-Gly-Arg-pNA [34].

In order to obtain a suitable diagnostic plot for the method of measurement of the invention, the enzyme initial concentration is chosen within a range of 10 to 1000 nM and is especially around 100 nM and the substrate concentration at zero time is chosen within the range of 50 to 5000 µM but not higher than 3 times the Km of the substrate and preferably below the Km.

The method of the invention is suitable for detecting or monitoring the function of the blood coagulation and fibrinolytic system. Especially, the invention provides a method which is suitable for detecting or monitoring a haemorrhagic disease or thrombotic disease or inborn or acquired tendencies to such diseases.

In a particular embodiment, this method is used for detecting or monitoring the interaction of determined substance(s) on thrombin activity in a whole blood or blood plasma sample, wherein said determined substance(s) have been administered to the sample donor or is (are) added to the sample to be assayed or is (are) added during thrombin generation.

The determined substance that may have an interaction on thrombin activity may especially be coagulation factors or drugs.

In a particular application of the method of the invention, this method is used for screening substances to determine their interacting capacity with thrombin generation.

In a specific embodiment of the invention, the method is used for measurement of the ETP of a whole blood or plasma sample. In another embodiment, the method of the invention is used for measurement of time to peak of thrombin.

In a further embodiment of the invention, the method is used for measurement of lag time in a sample.

In another embodiment, the method of the invention is carried out for measurement of the level of the peak of thrombin generated.

The invention also relates to a kit for carrying out the method of the invention, wherein said kit comprises:
  a determined amount of an enzyme for the preparation of a diagnostic plot;
  a determined amount of a substrate for said enzyme.

In a particular embodiment of the invention, the enzyme within the kit is thrombin and the kit further comprises tissue factor and calcium ions to enable thrombin generation.

In another particular embodiment of the invention, the kit comprises thrombin as the enzyme and instead of tissue factor it comprises an activator of the endogenous coagulation pathway. It then also comprises calcium ion to enable thrombin generation.

Further features and embodiments are disclosed in the examples and in the figures which follow.

LEGENDS TO THE FIGURES

FIG. 1: A simplified coagulation scheme.
Drawn arrows signify: converts into; small dashed arrows indicate feedback activation; Large dashed arrows indicatre feedback inhibition.
FIG. 2: A typical thrombin generation curve.
FIG. 3: Signal handling according to WO 03/093831.

Bold drawn line: signal from a fixed amount of added enzyme activity.
Thin drawn line: signal from an enzyme generated in situ.
Dashed bold line: Tangent to the thick bold line in the origin. For every value A of the generation experiment a corresponding value B is found on the calibrator curve. From this the corresponding value C is found on the extrapolated initial rate curve. The value of A that would be attained if substrate consumption and inner filter effect would not play a role is D, i.e. equal to C. Thrombin generation in the presence of a fluorogenic substrate under experimental conditions as described below.

FIG. 4: The diagnostic plot.
The underlying experiment is the conversion of the substrate by a fixed amount of enzyme that produces a signal (left frames, drawn lines). The velocity of increase of the signal (dF/dt) is plotted as circles. The dashed line is the enzyme potential ($\eta$) plotted as a function of time. This is a straight line because $\eta = E \cdot t$ and E is constant. In the right frame dF/dt and $\eta$ are plotted as a function of the signal (F). A straight line or a parabola is fitted through the dF/dt values. These fitted lines are plotted in the left frames (the lines fitting through the circles. The arrows indicate the point that the fit becomes incorrect and indicate the highest value of F ($F_{int}$) at which the method can be applied. From the dashed line it can be read up to which value of $\eta$ the method applies.

Figure 5A:
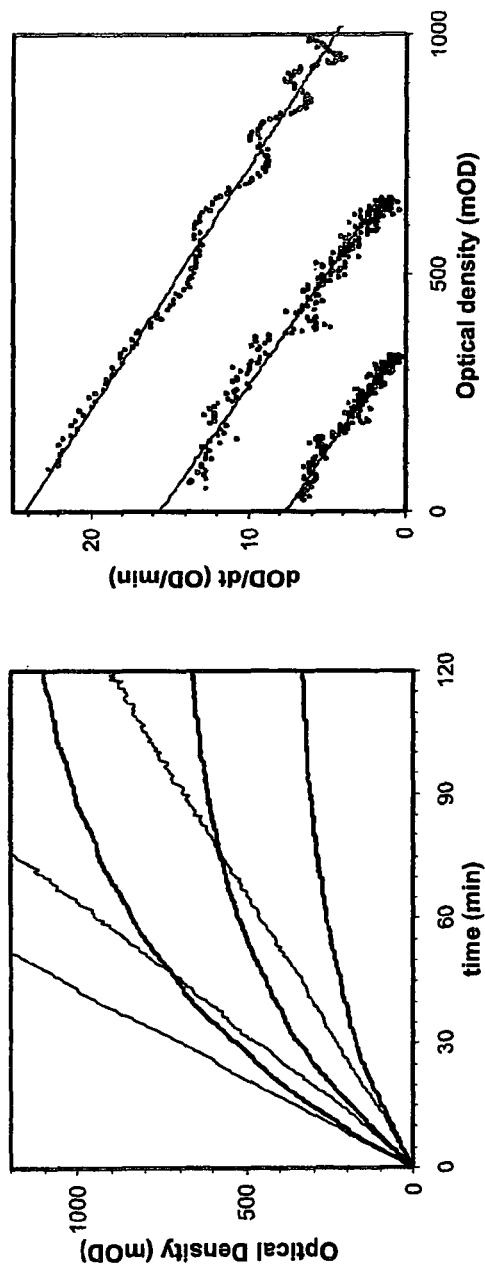

FIG. 5A: Signal v. time and dOD/dt v. OD plots from example 1.

Figure 5B:
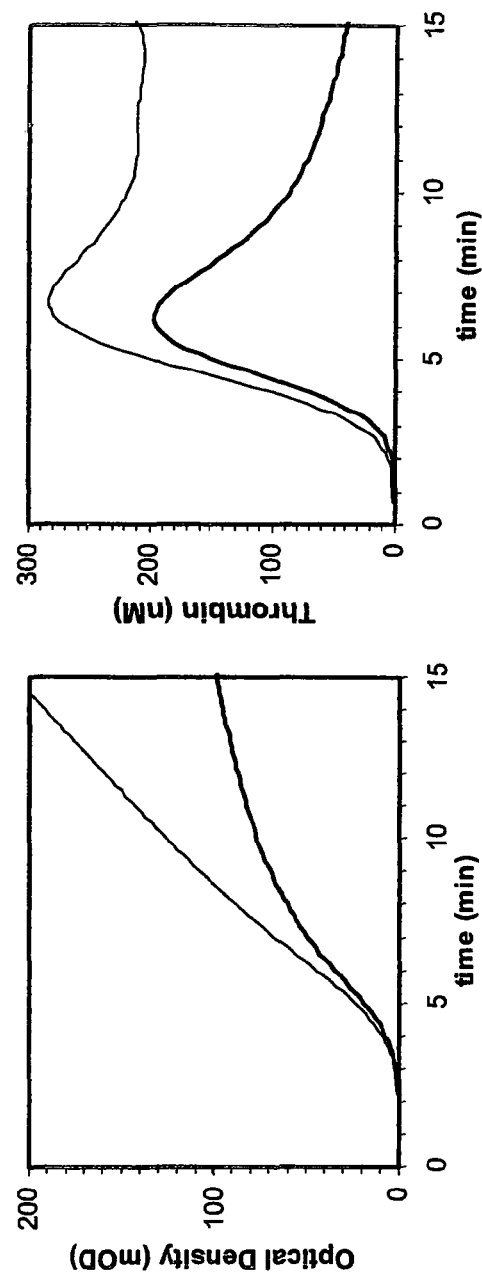

FIG. 5B: The thrombin generation experiment from example 1.
Left frame: Signal v. time plot, right frame, first derivatives. Bold lines: experimental signal, thin lines: corrected signal.

Figure 6A:
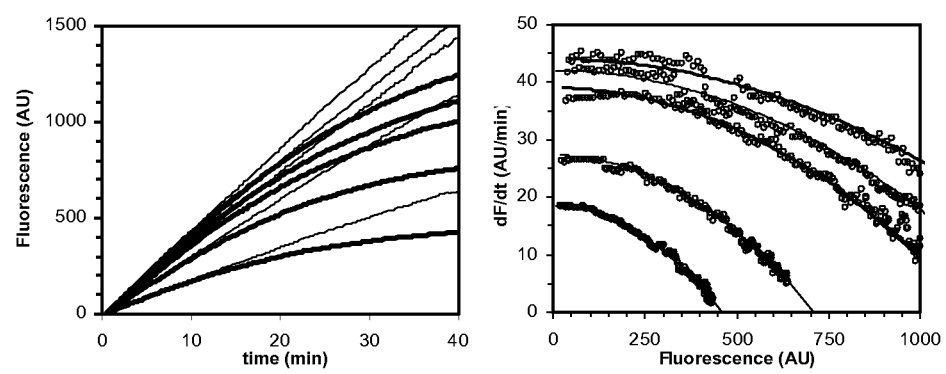

FIG. 6A: Signal v. time and dF/dt v. F plots from example 2.

Figure 6B:
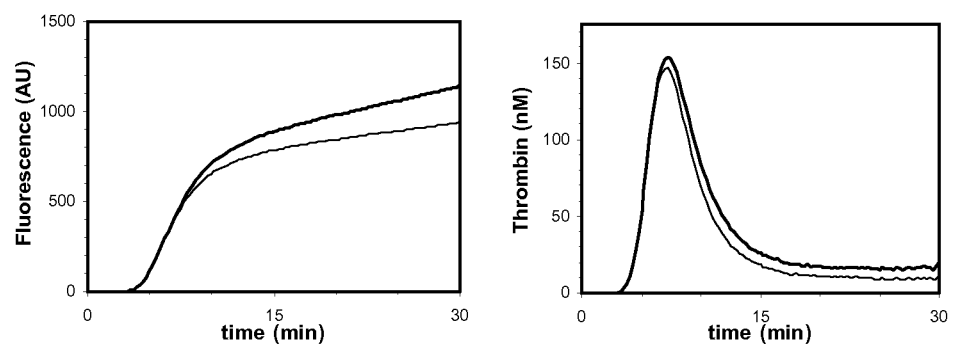

FIG. 6B: The thrombin generation experiment from example 2.
Left frame: Signal v. time plot, right frame, first derivatives. Bold lines: experimental signal, thin lines: corrected signal.

Figure 7:
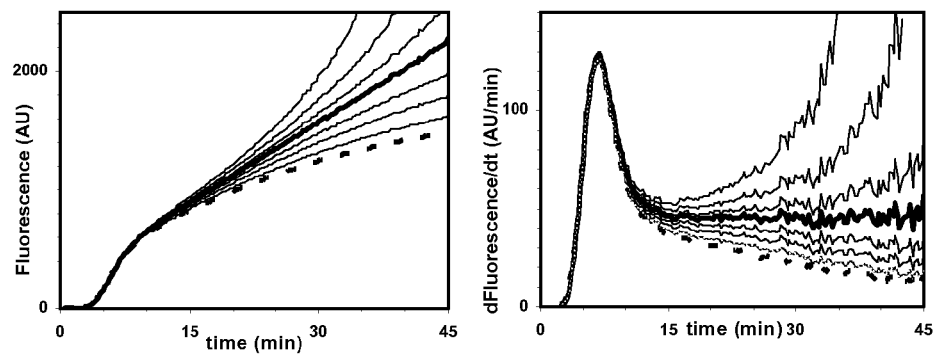

FIG. 7: The thrombin generation experiment from example 3.
Left frame: Signal v. time plot (dashed line) and corrected plot for various values of $\alpha$. Right frame, first derivatives. Bold lines: corrected plot for that value of $\alpha$ that renders the residual reaction velocity constant.

Figure 8:
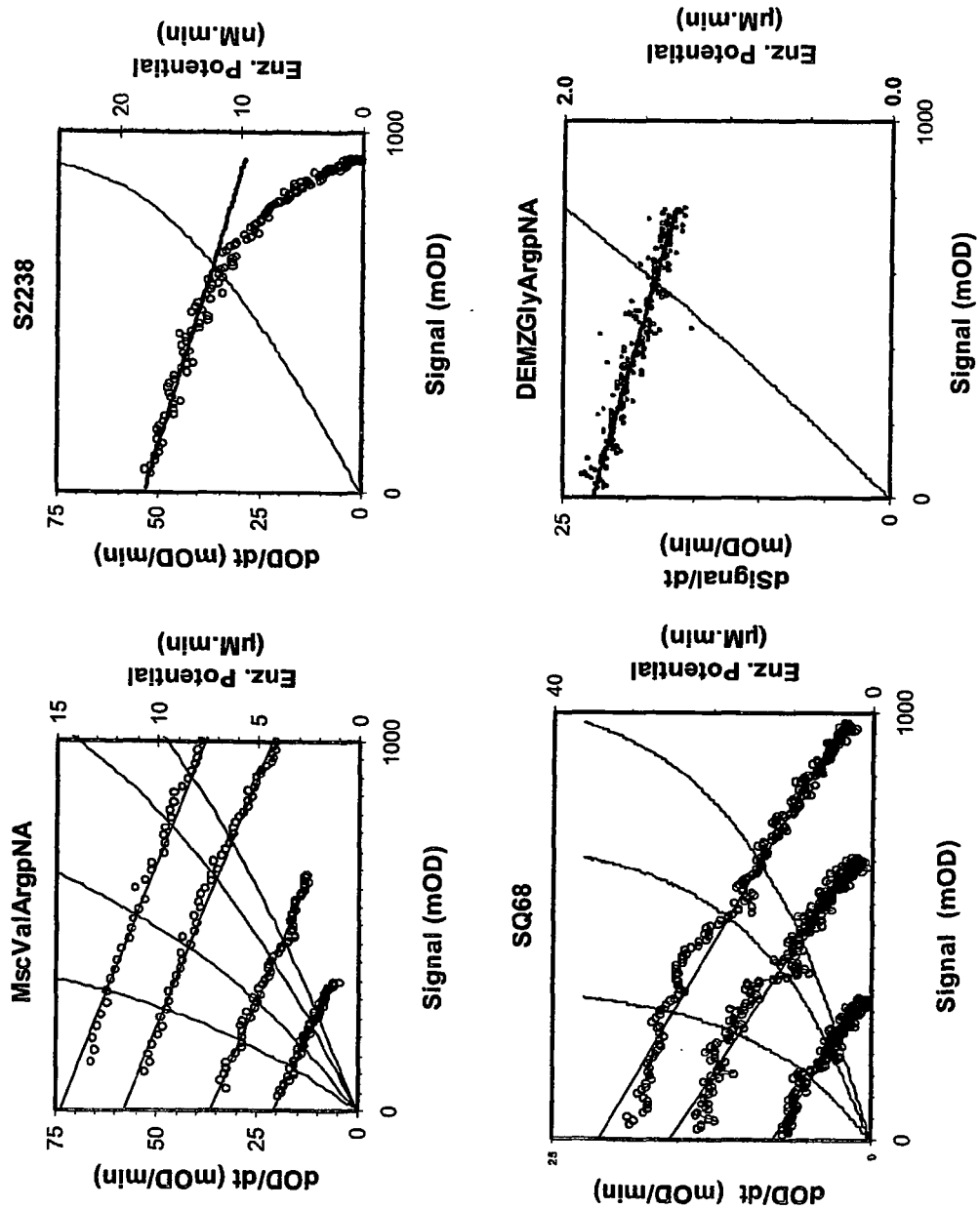

FIG. 8. Diagnostic plots for different chromogenic substrates. (belonging to expl. 4)

Figure 9:
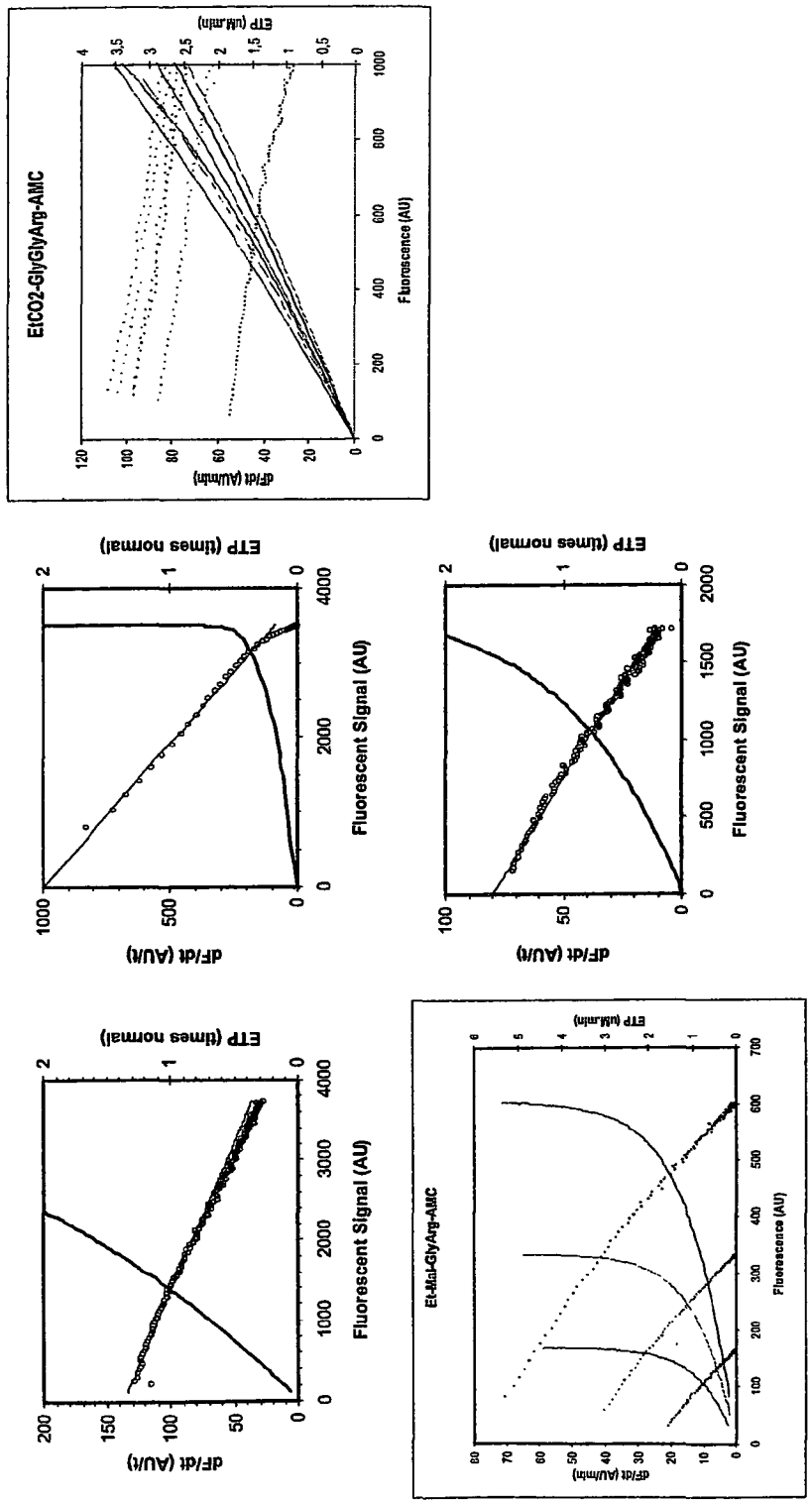

FIG. 9. Diagnostic plots for different fluorogenic substrates measured in bulk fluid. (belonging to expl. 5)

Figure 10:
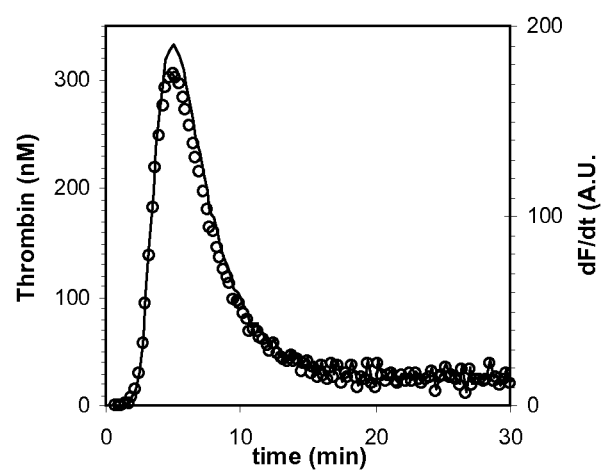

FIG. 10. Diagnostic plots for a fluorogenic substrate measured in a thin layer. (belonging to expl. 6).

Figure 11:
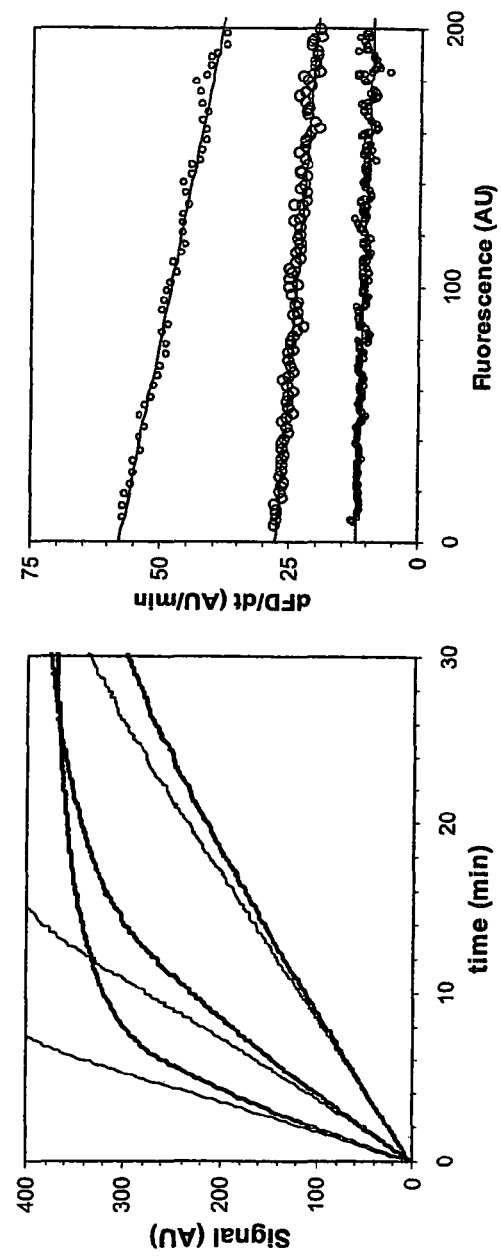

FIG. 11: A thrombin generation experiment in plasma in a thin layer (expl 6).
Left frame: Signal v. time plot and corrected plot. Right frame, first derivative of the corrected plot.

Figure 12:
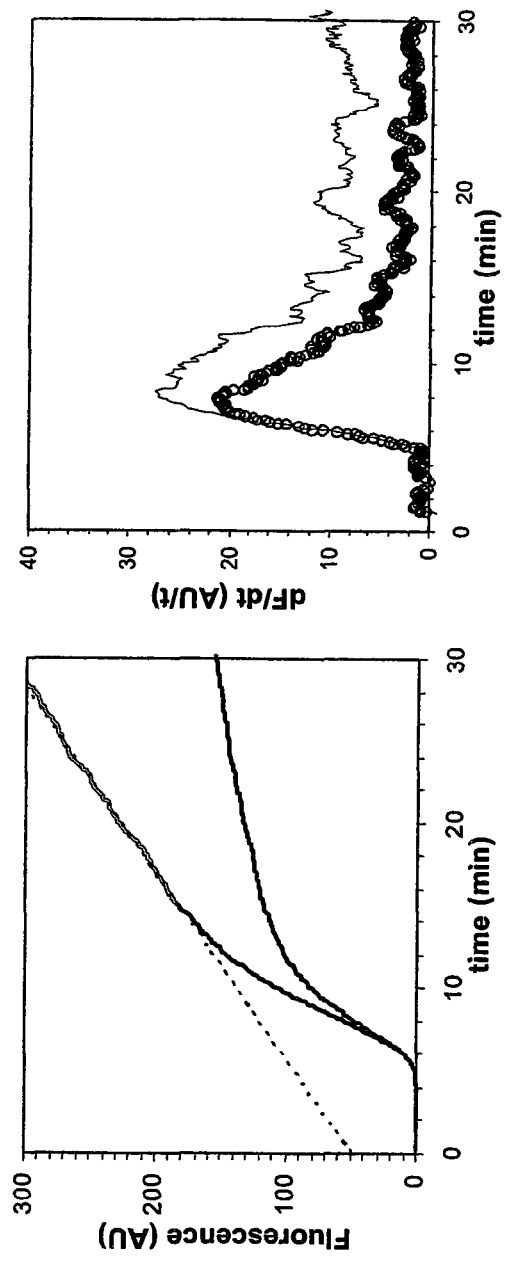
Figure 13:
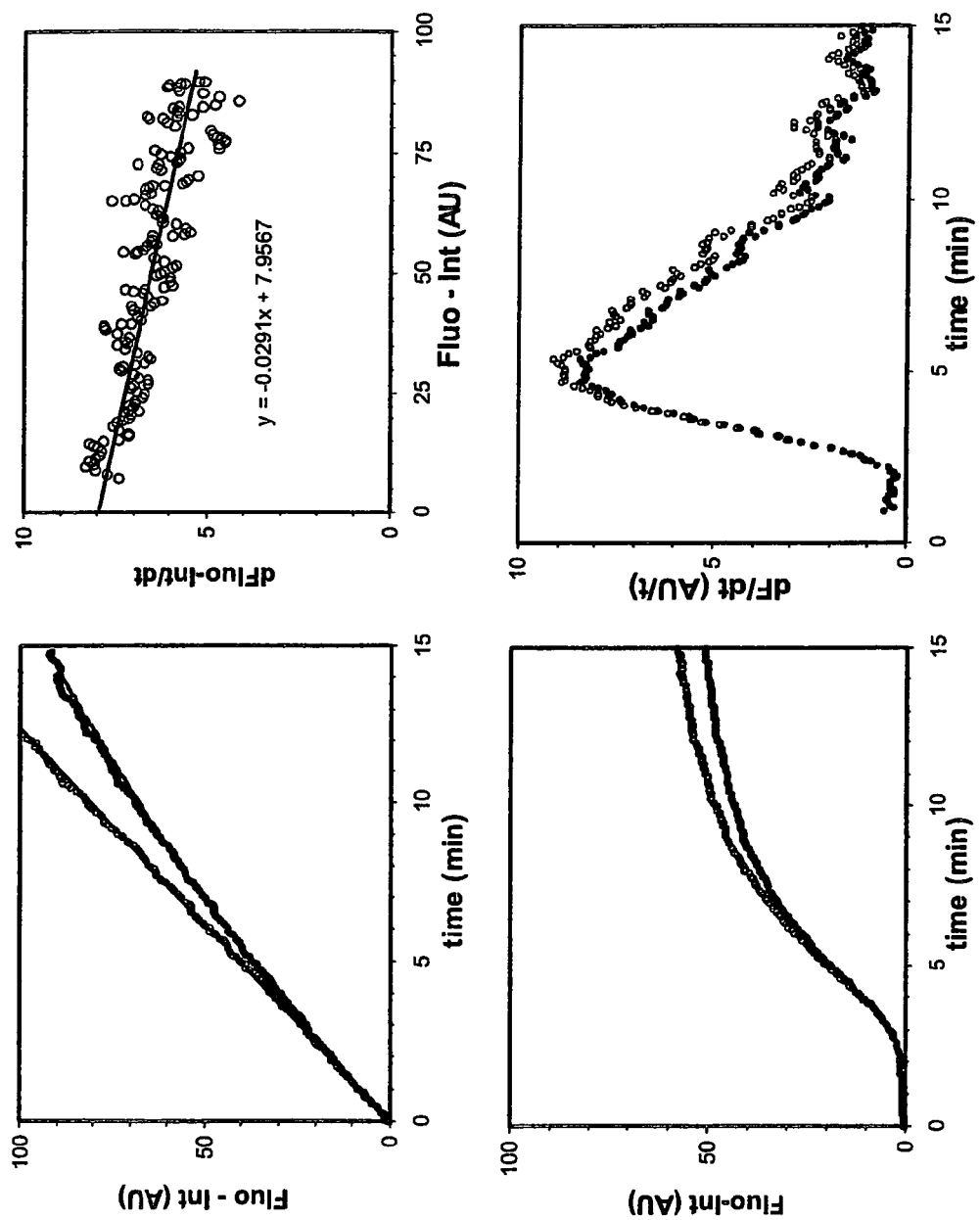

FIG. 12: A thrombin generation experiment in blood in a thin layer (expl 7).
Left frame: Signal v. time plots and corrected plots. Right upper frame: diagnostic plot. Right lower frame first derivative of the corresponding left frame.

DETAILED DESCRIPTION OF THE INVENTION

The present invention discloses a method to determine the exact course of an enzymatic activity ($E_{expt} = g(t)$) that develops and/or disappears in a reaction mixture and in which the enzymatic activity is probed through the monitoring of the signal from a reaction product ($F_{expt} = f(t)$) of an added substrate of that enzyme, independent of changes in the ratio between enzyme concentration and reaction velocity due to confounding factors such as substrate consumption, product inhibition, non-linearity between product concentration and the monitoring signal and others. The method described enables to calculate the course of enzyme concentration in time, despite such confounders up to a certain and well defined fraction of the substrate being consumed. It thus defines the concentration ranges of substrate where it is applicable and relates to the use of substrates for this purpose within these ranges.

The first step of the method is a diagnostic procedure. This step needs only to be carried out once for a defined experimental setup. In this procedure a fixed known amount of enzyme is monitored under identical conditions as the intended enzyme generation experiment (as to substrate concentration, composition of the reaction medium, temperature etc.). From the resulting time curve of signal ($F_{diagn} = f(t)$) a plot of $dF_{diagn}/dt$ against F is constructed (the "diagnostic plot").

Unexpectedly it was found that this plot is either a parabola or a straight line, either over the entire range of signal measured ($F_0$ to $F_{max}$) or up to a certain limit ($F_0$ to $F_{lim} < F_{max}$). If and in so far as the diagnostic plot is a straight line (dF(t)/dt = $v_{init}(1 - F(t)/\alpha)$) the signal ($F_{ideal}$) that would have been obtained if no confounding factors would have been present can be calculated as $F_{ideal} = -\alpha \ln(1 - F_{exp}/\alpha)$ and the enzyme concentration in the course of time can be found as $E(t) = v_{init} \cdot dF_{ideal}/dt$.

If and in so far as the diagnostic plot is a parabola (dF/dt = $v_{init}(1 - (F_{diagn}/\alpha)^2)$), $F_{ideal}$ can be found from $F_{ideal} = \alpha \cdot \text{arctan h}(F_{exp}/\alpha)$ (arctan h is the inverse function of the hyperbolic tangent). Again the enzyme concentration in the course of time can be found as $E(t) = v_{init} \cdot dF_{ideal}/dt$. These equations hold for any experimental data obtained under identical conditions as the diagnostic plot and in so far as $F \leq F_{lim}$.

Application of these equations requires prior determination of the constants $v_{init}$ and $\alpha$ and the limit of applicability $F_{lim}$. The constant $v_{init}$ is the initial reaction velocity (dF/dt at F=0) and can be determined under initial conditions by any method known to the art. The constant $\alpha$ is the maximal signal that can be obtained when the reaction runs to completion if $F_{lim} = F_{max}$ and can be found as the intercept with the abscissa of the diagnostic function ((dF(t)/dt = $v_{init}(1 - F(t)/\alpha)$ or dF/dt = $v_{init}(1 - (F_{diagn}/\alpha)^2)$ in case that $F_{lim} < F_{max}$.

The parameter $\alpha$, when entered into the above equations will, at constant enzyme activity, render values for dF/dt that remain constant in time. Consequently, if in the course of an experiment a time period occurs during which the enzymatic activity does not change, $\alpha$ can be found experimentally as the value that renders dF/dt constant during that period. Constant enzymatic activity is found, logically, under conditions of determination of the diagnostic plot but also e.g. at the end of a thrombin generation experiment in plasma, when part of the generated thrombin is bound to $\alpha_2 M$ to form the stable $\alpha_2 M$-thrombin complex (see also examples).

In the experiment for the establishment of the diagnostic plot, E is constant, so that the course of the enzyme potential $\eta = E \cdot t$ is known and can be plotted as a function of F (FIG. 4, dotted lines). This allows to determine the value of $\eta$ corresponding to $F_{lim}$ and thus to judge up to what values of $\eta$ ($\eta_{lim}$) the method disclosed can be applied with confidence. This defines the class of useful substrates as those for which $\eta_{lim}$ is larger than the value to be expected in a given experimental setup.

Inversely, a useful substrate in a useful concentration range can be defined as that substrate in that concentration range that renders a diagnostic plot that is either a straight line or a hyperbola and the $\eta_{lim}$ of which is larger than the enzyme potential to be determined.

The method revealed is particularly useful for the determination of the course of thrombin or plasmin in coagulating and lysing blood. According to prior art, conversion of the signal curve into a curve of the course of thrombin- or plasmin-activity requires continuous comparison to an activity curve obtained with a known amount of fixed thrombin- or plasmin activity, and a step-by-step digital calculation procedure. The present method offers an analytical algorithm and abolishes the necessity of a simultaneous calibration curve.

Experimental Part and General Features to Carry Out the Invention.

In the figures, fluorescence intensity is expressed in normalised units (N.U.), i.e. the initial rate of fluorescence production by 100 nM of thrombin activity is set to 1 N.U./min. In this way the initial conditions are standardised and we can restrict the discussion to the essential question, the variability of the calibration factor in time.

The method according to the invention is a two step procedure:

In a first step a diagnostic experiment is carried out to find the nature and the constants of the equation that applies in a given experimental situation. In a second step experimental data from an enzyme generation experiment are transformed into a quantitatively correct enzyme generation curve via the equation found. This diagnostic plot has to made only once for every intended experimental setup.

First Step: The Diagnostic Plot

To obtain the diagnostic plot, the course of signal (F) at a fixed, known but arbitrary enzyme activity is measured under exactly the same conditions as are to be encountered in the enzyme generation experiment (e.g. substrate kind and concentration, plasma dilution, buffer composition, dimensions of the reaction vessel), if possible until the substrate is exhausted ($F=F_{end}$). Then a plot is made of the first derivative of the signal (dF/dt) against the signal ($F_{obs}$), Unexpectedly we found that either over the entire range of values measured or up to a given limit of F ($F_{lim} \leq F_{end}$) this plot, in excellent approximation, is either a straight line or a parabola. In both cases the highest value, i.e. the true initial reaction rate, is found at the intercept with the ordinate because dF/dt is maximal when no substrate has been consumed ($S_t \approx S_0$) and not enough product has appeared to disturb the assessment of further product.

So up to the value $F_{lim}$, the graph is either of the form $dF/dt = v_{init}(1-F/\alpha)$ or of the form $dF/dt = v_{init}(1-(F/\alpha)^2)$. In both cases the constants $v_{init}$ and $\alpha$ can be obtained from the diagnostic graph (see examples). These constants are needed for the transformation of the data into correct enzyme concentrations.

Second Step: Transformation of the Experimental Data.

If, and in so far as, the graph of dF/dt against F in the diagnostic plot is a straight line (e.g. example 1) any experimental value of F ($F_{exp}$) can be transformed into a corresponding "ideal" value ($F_{trf}$) by the transformation $F_{trf} = -\alpha \ln(1-F_{exp}/\alpha)$. The enzyme generation graph can then be found as $E(t) = v_{init}(dF_{trf}/dt) = v_{init}(d(-\alpha \ln(1-F_{exp}/\alpha))/dt$. This can be checked by applying the formula to the $F_{exp} = f(t)$ data in the diagnostic plot, which should render a straight line, within the limits of experimental scatter.

If, and in so far as, in the diagnostic plot dF/dt against F is a parabola (e.g. example 2) any experimental value of F ($F_{expt}$) can be transformed into a corresponding "ideal" value by the transformation $F_{trf} = \alpha \operatorname{arctan h}(F_{expt}/\alpha)$. The enzyme generation curve can then be found as $E(t) = v_{init}(dF_{trf}/dt) = v_{init}(d(\alpha \operatorname{arctan h}(F_{exp}/\alpha))/dt)$. This can again be checked by applying the formula to the $F_{exp} = f(t)$ data, which should render a straight line, within the limits of experimental scatter.

There are alternative methods to obtain the constants $v_{init}$ and $\alpha$; $v_{init}$ is the rate of substrate conversion under initial conditions and can be found by any method known to the art, e.g. the standard methods of initial rate enzymology.

The constant $\alpha$ can be found experimentally by trial and error, because the correct value is the one that transforms into a straight line any experimental curve that is obtained at constant enzyme concentration. In practice there are two situations that lend themselves to this purpose. The first one is the experiment at the basis of the diagnostic plot, i.e. measuring $F_{expt}$ at constant enzyme activity (examples 1 and 2). The other is that part of an experimental curve where it is known that the enzyme activity is constant. This is the case in experiments carried out in blood plasma. A proteolytic enzyme formed in blood plasma will bind to plasmatic enzyme inhibitors, under which $\alpha_2$M. With this inhibitor it forms a stable complex without biological activity but that is still capable of splitting the added substrate. In a thrombin generation curve e.g. at the end of the experiment, when free thrombin has disappeared, a fixed residual activity of $\alpha_2$M-thrombin formed during the thrombin generation process remains. In that case the correct value of $\alpha$ is the one that transforms the last part of the experimental data into a straight line and the slope of that line divided by the amidolytic activity at the end of the experiment gives $v_{init}$ at unit enzyme concentration (example 3).

It should be noted that, in fluorimetric experiments, $v_{init}$ is dependent upon the observed rate of the reaction and hence on the colour of the sample whereas ($=\alpha/v_{init}$) is not. This makes that, in series of samples in which the fluorescent yield varies due to differences in quenching between samples, it suffices to calculate $v_{init.unknow}$ for each individual sample by measuring the quenching in that sample and its ratio (R) to the quenching in a plasma with known $V_{init}$, so that $v_{init.unknow} = R \cdot v_{init.known}$. R can be found by any of a number of methods known to the art, i.e by measuring $Cf_0$, by measuring the optical density or by measuring the fluorescent yield of a fixed amount of fluorophore.

It is stressed that the method is an empirical method, found via a surprising observation, and that it can be applied only in so far as $F < F_{limit}$. Whether $F_{limit}$ is sufficiently high for practical purposes depends upon the enzymatic activity that is to be expected in the experiments and needs to be determined for each practical application.

In experiments where the active enzyme is transiently present (e.g. thrombin and plasmin generation curves) the area under the enzyme-time curve gives the enzyme potential ($\eta = E \cdot t$) and thus the extend of enzyme consumption that is to be expected. Due to competition between the substrate and natural enzyme inhibitors, this area under the curve as a rule is increased by the presence of substrate. When in the absence of substrate it would be $\eta_0$, then, in the presence of a concentration S of a substrate with a Michaelis constant of Km the area under the curve increases to $\eta_s = \eta_0 \cdot (Km+S)/Km$. For the measurement to be correctly carried out according to the present disclosure $\eta$ at $F=F_{lim}$ should be $> \eta_s$, The recognition of these limits defines the range of practical usefulness of substrates and claims the use of such substrates in this range.

EXAMPLES

Materials and Methods

Chemicals

Ancrod, the fibrinogen clotting enzyme of the Malayan Pit Viper, was the commercial preparation Arvin (Knoll AG, Ludwigshafen, Germany).

Malonyl-α-aminoisobutyryl-arginine para-nitroanilide methyl ester-HCl (SQ68) was synthesized by Diagnostica Stago, France.

Phospholipids consisted of a mixtures of 20 mol % phosphatidylserine, 20 mol % phosphatidyl-ethanolamine and 60 mol % phosphatidyl-choline (Avanti, Alabaster, Ala., USA).

Recombinant relipidated tissue factor (rTF) not containing polybrene or $Ca^{++}$ was a kind gift from Dade Behring (Marburg, Germany).

Staphylocoagulase-thrombin was prepared by mixing equimolar amounts of these two proteins.

All other chemical were commercially obtained at the highest available grade of purity.

Reagents

Buffers: Two buffers are used: 'BSA5' for preparing dilutions of the reagents and 'BSA60' for the dissolution of substrates that do not solve readily in aqueous medium. BSA5 contains 20 mM Hepes, 140 mM NaCl, 0.02% $NaN_3$ and 5 mg/mL BSA at pH 7.35. BSA60 contains 20 mM Hepes, 0.02% $NaN_3$ and 60 mg/mL BSA at pH 7.35. To dissolve BSA it is brought on top of the buffer without stirring to allow it to dissolve slowly. This can take more than an hour. Next the buffer is filtered using a corning filter system 255 mL with 0.2 μm PES membrane. The buffers are stored in the freezer at −20° C. They are kept at room temperature during an experiment.

Phospholipids (PL) The phospholipid suspension was obtained by sonication of the required amount of phospholipids for 2×5 min. in cooled hepes buffer so as to obtain a concentration of 24 μM. The stocks are stored at −80° C. and kept at room temperature during an experiment.

A fresh mixture of fluorescence substrate and $CaCl_2$ (FluCa) was prepared for each fluorescence experiment as follows: to 875 μl of buffer, 100 μl of 1 M $CaCl_2$ was added, at 37° C., 25 μl of a DMSO solution of the required concentration of the fluorogenic or chromogenic substrate was then squirted in and immediately vigorously mixed.

Trigger solution for the extrinsic system contains about 300 pM rTF and 4 μM procoagulant phospholipids in Hepes buffer A.

Trigger solution for the intrinsic system contains 1: 25 diluted Actin FS® and 4 μM procoagulant phospholipids in Hepes-buffer A.

Blood and Plasma

Blood was obtained through antecubital venipuncture (1 volume trisodium citrate 0.13 M to 9 volumes blood) from healthy consenting individuals. Free flow or minimal suction was employed; vacuum containers were avoided.

Platelet rich plasma (PRP) was collected from the upper ¾ volume of plasma supernatant, after centrifugation at 265×g for 10 min at room temperature. The platelets were counted (Beckman Coulter counter) and PRP was adjusted to $150 \times 10^9$ platelets/L with its own platelet poor plasma (PPP). PRP was always used within 1 h after venipuncture.

PPP is prepared by centrifuging twice at 2900 g for 10 min at room temperature. In order to avoid contamination with procoagulant microparticles from aging platelets, PPP is prepared within 30 min after venipuncture.

Defibrinated PPP:

Ancrod is added to PPP so as to reach a final concentration of 1 U/mL. The plasma is mixed well (vortex) and kept at 37° C. for 10 minutes. Then it is put on ice for 10 minutes. To remove the clot one has to turn very slowly with a spoon against the wall of the tube and take out the clot. Because Ancrod does not cause haemolysis, it can also be added to whole blood, rendering defibrinated plasma directly upon centrifugation.

Preparation with stable thrombin-like activity ($\alpha_2$M-thrombin)

In order to obtain a stable thrombin-like activity in plasma, we used $\alpha_2$M-thrombin, prepared as described previously [22].

Optical Density Based Method for Thrombin Activity:

A suitable chromogenic substrate, i.e. a substrate from which a chromogenic group is split when acted upon by the enzyme to be measured (thrombin, plasmin etc), is added to the reaction mixture. Unless otherwise indicated, for thrombin generation, this mixture consists of four parts of defibrinated plasma, one part of trigger solution and one part of start solution. The reactions can be carried out in a spectrophotometer cuvette, a 96 well plate to be read in a photometric well-plate reader or in a laboratory automaton as e.g. the Cobas Bio and Cobas Fara centrifugal analysers (F. Hoffmann-La Roche, Basel, Switzerland). In short in any device capable of measuring the optical density at 405 nm at 30 s intervals during 10 to 30 min.

Typically 80 μL of defibrinated plasma with 20 μL of rTF without Ca2+ are incubated at 37° C., during a time sufficient for temperature equilibration. Thrombin generation is started by adding 20 μL of a pre-warmed start solution containing 100 mM $CaCl_2$ and 3 mM substrate. After the start of the reaction the optical density at 405 nm is recorded at intervals of maximally 30 s for the time required (≥15 min). Depending upon the measuring device a multiple of the volumes can be used.

Fluorescence Based Measurement of Thrombin Activity.

The development of fluorescence intensity from aminomethylcoumarine (AMC) is typically measured in a 96-well plate fluorometer (Ascent reader, Thermolabsystems OY, Helsinki Finland) equipped with a 390/460 filter set (excitation/emission) and a dispenser. Immulon 2HB, round-bottom 96-well plates (Dynex) are used. Minimally four readings are done per minute and experiments are carried out in quadruplicate unless otherwise indicated.

To each well, 80 μl of plasma is added. Wells in which TG is measured receive 20 μl of buffer, containing the trigger but no $Ca^{2+}$.

Wells in which constant thrombin-like activity is to be measured receive 20 μl of the $\alpha_2$M-thrombin solution at the required concentration as indicated. For PPP, the trigger is 30 pM of recombinant tissue factor (TF) and 24 μM phosphatidyl-serine/phosphatidyl-choline/phosphatidyl-ethanolamine vesicles in Hepes-buffered saline. For PRP the trigger is 20 μl of 3 pM of rTF without added PL.

The plate is placed in the fluorometer and allowed to warm to 37° C. (minimally 15 min). The dispenser of the fluorometer is flushed with warm 100 mM CaCl2 solution, emptied, and then flushed with a prewarmed (37° C.) solution of the substrate in Hepes buffer with 60 g/L bovine serum albumin (FluCa). At the start of the experiment, the instrument dispenses 20 μl of FluCa to all the wells to be measured, registers this as zero time, shakes them for 10 s and starts reading.

Data Handling

The raw data of optical density or fluorescence measurements of thrombin activity were exported to SIGMAPLOT version 9.0 (Systat Software Inc., Point Richmond, Calif., USA) or to EXCEL (Microsoft® Excel 2002 or higher) for further mathematical operations.

EXAMPLES

Example 1

Calculation of Thrombin Activity from the Conversion of the Chromogenic Substrate MZ-Aib-Arg-pNA.HCl (SQ68)

Step 1: Diagnostic Plot, Determination of Constants.
Reaction mixture: See under methods. Enzyme: 400 nM $\alpha_2$M-thrombin, Substrate: 50-100-150 μM SQ68. The results are shown in FIG. 5A, left frame. The diagnostic plot constructed with these data in the right frame of the same figure. The straight line relationship in the diagnostic plot indicates that the curved lines obtained at constant enzyme activity (left frame, bold lines) can be transformed into straight lines (left frame, thin lines) by applying the formula $OD_{trans}=-\alpha \ln(1-OD_{exp}/\alpha)$, where $\alpha$ is found as the intercept of the straight lines with the abscissa in the right frame. This is verified by the straight lines that are obtained when this transformation is carried out on the original data (left frame, thin lines)
Step 2: Determination of a Thrombin Generation Curve.
Reaction mixture: see under methods, extrinsic thrombin generation trigger, 50 μM SQ68. The results are shown in FIG. 5B, left frame.

The bold line gives the experimental OD-trace, the thin line the same data transformed by $OD_{trans}=-\alpha \ln(1-OD_{exp}/\alpha)$. The right frame shows the thrombin generation curves, obtained as first derivatives of the curves in the left frame, scaled with the initial velocity read in the upper right frame. The intercept with the ordinate of the 50 μM line in the diagnostic plot giving the dOD/dt that is caused under initial conditions by 400 nM α2M-thrombin. Alternatively the scaling can be done by measuring the thrombin activity of a sample of the remaining reaction mixture on S2238. This thrombin concentration than is the activity that causes the end velocity of the transformed curve in the left frame, i.e. the end level of the corresponding first derivative in the right frame. In the present case the activity found was 198 nM, i.e. within 10% of the level with the first approach.

Example 2

Calculation of Thrombin Activity from the Conversion of the Fluorogenic Substrate ZGGR-AMC, Using Constants Determined in a Diagnostic Plot Step 1: Diagnostic Plot, Determination of Constants.
Reaction mixture: See methods. Substrate ZGGR-AMC in the final concentrations of 83-166-250-333-500 μM, enzyme 100 nM α2M-thrombin.
The results are shown in FIG. 6A, left frame. The diagnostic plot constructed with these data in the right frame of the same figure. The parabolic relationship in the diagnostic plot indicates that the curved lines obtained at constant enzyme activity (left frame, bold lines) can be transformed into straight lines (left frame, thin lines) by applying the formula $F_{trans}=\alpha \text{ arctan h}(F_{exp}/\alpha)$, where $\alpha$ is found from the intercept of the parabolas with the abscissa in the right frame. This is verified by the straight lines that are obtained when this transformation is carried out on the original data (left frame, thin lines)

Step 2
Determination of a Thrombin Generation Curve.
Reaction mixture: See under methods, extrinsic thrombin generation trigger; final concentration of Z-GGR-AMC: 250 μM. The fluorescence trace is shown in FIG. 6B, left frame. The thin line gives the experimental OD-trace, the bold one the same data transformed by $F_{trans}=\alpha \text{ arctan h}(F_{exp}/\alpha)$. The right frame shows the thrombin generation curves, obtained as first derivatives of the curves in the left frame, scaled with the initial velocity read in the upper right frame, as in example 1. Again the scaling can be alternatively done by measuring the thrombin activity of a sample of the remaining reaction mixture on S2238 (16.7 nM).

Example 3

Calculation of Thrombin Activity From the Conversion of the Fluorogenic Substrate ZGGR-AMC, Without Simultaneous Calibration, Using the End Level of $\alpha_2$M-thrombin Reaction mixture: Defibrinated plasma, extrinsic clotting system triggered. See further under methods. The experiment at 416 μM final concentration ZGGR-AMC is shown in FIG. 7. Similar results were obtained at 83, 166, 250 and 333 nM substrate. Because both substrate consumption and inner filter effect pay a role, the formula $F_{trans}=\alpha \text{ arctan h}(F_{exp}/\alpha)$ is applied to the experimental data (loft frame dashed line). Different values of $\alpha$ are entered to find that value that transforms the tail of the fluorescence data into a straight line; knowing that it should be a straight line because the enzyme activity is stable, endogenously generated, α2M-thrombin. A horizontal endline of the first derivative (right frame) obviously serves the same purpose and is easier to judge. The conversion of dF/dt to nM thrombin can be carried out, as in examples 1 and 2, by measuring the thrombin activity in the remaining fluid by any method known to the art. In the present example the final slope of the correctly transformed line is 43.6 AU/min. A sample of the reaction mixture showed an amidolytic activity equivalent to 69.3 nM thrombin. The conversion factor from dF/dt (FIG. 11, right frame) into nM thrombin in this case therefore was 69.3/43.6=1.59.

In this example defibrinated plasma was used because much more $\alpha_2$M– forms in the absence of fibrinogen than in its presence, but this is not required for application of this method.

Example 4

Definition of Substrates for Thrombin Monitoring on Basis of the Diagnostic Plot; Chromogenic Substrates This example shows the diagnostic plots with different chromogenic substrates for thrombin and how these can be used to judge whether they can be used to determine a thrombin generation curve (FIG. 8).

In general, a substrate can be used for correct thrombin monitoring if the approximation used by the method revealed in the present disclosure holds over the range of substrate consumed during the experiment. This amount is determined by the maximal enzyme potential (η) that to be expected in the experiments. As explained in the bulk text, in thrombin generation experiments this is 1.5 (Km+S)/Km (paragraph 043). In the experiment to obtain the diagnostic plot the enzyme concentration (E) is constant and known. So the enzyme potential (η) is known and can be rendered In the diagnostic plot (curved thin lines in FIG. 8).

In FIG. 8 the open circles are the experimental values obtained at the concentrations of substrate and enzyme indicated in the following table.

| Substrate | Abr. | Km µM | S µM | E nM | η µM · min | limit nM · min |
|---|---|---|---|---|---|---|
| HD-Phe-Pip-Arg-pNA | S2238 | 10 | 100 | 0.4 | 11 | 0.014 |
| DEMZ-Gly-Arg-pNA | DEMZ | 866 | 500 | 50 | 1.58 | >2 |
| Msc-Val-Arg-pNA | MSC | 882 | 50 | 250 | 1.06 | >15 |
|  | MSC | 882 | 100 | 250 | 1.11 | >15 |
|  | MSC | 882 | 150 | 250 | 1.17 | >15 |
| MZ-Aib-Arg-pNA | SQ68 | 830 | 50 | 300 | 1.06 | >30 |
|  | SQ68 | 830 | 100 | 300 | 1.12 | >30 |
|  | SQ68 | 830 | 150 | 300 | 1.18 | >30 |

In this table η indicates the enzyme potential that is to be expected in the thrombingeneration experiment and limit indicates the limit of enzyme potential that can be measured with the indicated substrate at the indicated concentration.

(NB: The Km values have been obtained in buffer and not in plasma but any value of Km between 0.5 and 2 times the present one would have allowed similar conclusions as to the suitability in thrombingenration experiments)

In FIG. 8 it is seen that straight lines fit through the data over the whole range of ODs measured for three of the four substrates tested. For one (S2238) the straight line fits only up to mOD~650. At that OD the enzyme potential can be read from the plot to be ~12.5 nM.min, whereas the ETP to be measured in the presence of this substrate, due to the tight binding and the ensuing inhibition of natural antithrombins is 11000 nM.min (table). This substrate therefore is unsuitable for the measurement of thrombin generation. Comparable analysis for the other substrates show that they are suitable (Table 1).

Example 5

Definition of Substrates for Thrombin Monitoring on Basis of the Diagnostic Plot; Fluorogenic Substrates A similar approach as that of example 4 can be applied to fluorogenic substrates. The substrates, previously described in ref [35] were, from left to right are BZ-Phe-Val-Arg-AMC, Z-Gly-Pro-Arg-AMC and Z-Pro-Arg-AMC, all tested at a concentration of 1 mM in the setup described under methods.

From the diagnostic plot it can be seen that BZ-Phe-Val-Arg-AMC and Z-Pro-Arg-AMC can be used for the measurement of thrombin generation. Z-Gly-Pro-Arg-AMC has a turnover number that is so high as to have the substrate consumed before thrombin generation is over. The scaling factor necessary to convert the arbitrary dF/dt values into nM thrombin is derived from the measurement of the amidolytic activity on a thrombin substrate of the material remaining after thrombin generation is over, as in example 3.

Example 6

Calculation of Thrombin Generation Measured in a Thin Layer

The experiments of this example were executed with plasma absorbed onto a cellulose matrix (Whatman filter paper 1 (Schleicher & Schuell, UK)) covered with optically clear tape. Fluorescence is measured in a high sensitivity fluorescence spectrometer, from Ocean Optics Inc, (Dunedin, Fla., USA), model USB 4000.

A mixture of normal plasma (66 µL), 416 µM of Z-Gly-Gly-Arg-AMC in buffer (33 µL) and 33 µL of a solution of staphylocoagulase-thrombin containing 2.5 mM of Gly-Pro-Arg-Pro was absorbed into the matrix. The staphylocoagulase-thrombin clots the plasma but clotting during handling and before absorption was retarded by the added polymerization inhibitor Gly-Pro-Arg-Pro. The enzyme also converts the substrate and with the same kinetic constants as free thrombin ([36]. Three concentrations of this enzyme were used: 100 nM (upper lines), 50 nM (middle lines), 25 nM (lower lines).

The fluorescence was recorded and a diagnostic plot of dF/dt against F was constructed. FIG. 10, left frame, shows fluorescence measurements (thick lines) and transformations of the measurements (thin lines). The right frame shows the diagnostic plots obtained from the data of the left frame. It is seen that the diagnostic plots are straight lines, probably because in a thin layer the inner filter effect does not complicate the measurement and only substrate consumption is a confounding factor.

In FIG. 11 the results are shown of an experiment in which 100 µL of a thrombin generating plasma mixture (prepared as indicated under methods, extrinsic system), was absorbed in filter paper and measured as above. The lower line in the left frame gives the experimental data and the upper line (with a linear trend-line fitted to the right hand part) gives the transformed data. The correct value of a was obtained as in example 3. The right hand frame gives the first derivative of the original fluorescence data (circles) and of the transformed data (thin line).

Because the diagnostic plot was linear (FIG. 10, right frame), the transformation into ideal values was carried out with the logarithmic formula as described above. The value of α was found by trial and error, as in example 3. The small signal has a relatively large experimental scatter and hence a "noisy" first derivative. In practice mathematical curve fitting techniques can be applied to obtain smooth curves.

Example 7

Calculation of Thrombin Generation Measured in Whole Blood

FIG. 12 shows the results of measurement in whole blood adsorbed onto a filter paper, in a way identical to the plasma sample in example 6.

The calibrator experiments are shown in the upper frames. The following procedure was used: To 30 µL of citrated blood is added 10 µL of Z-Gly-Gly-Arg-AMC (2.5 µM) and 20 µL of a solution containing staphylocoagulase-thrombin (0.22 nM) and the polymerisation inhibitor Gly-Pro-Arg-Pro (2.5 mM). The fluorescence data are shown in the left-hand frame (lower curve). The diagnostic plot is shown in the right-hand frame. The upper straight line in the left frame is the transformed data, using the logarithmic formula and α read from the diagnostic plot.

The lower frames in FIG. 12 show a thrombin generation experiment in whole blood. The reaction procedure was: In 100 µL of citrated whole blood thrombin generation is started by adding 20 µL of a solution with Z-Gly-Gly-Arg-AMC (2.5 mM), CaCl$_2$ (100 mM) and soluble relipidated recombinant tissue factor (30 pM). After mixing, 5 µL of the blood-reagent mixture is immediately transferred to the cellulose matrix and fluorescence measurement started.

The calibrator curve is shown in the left upper frame (lower, curved line). From this the diagnostic plot is constructed (upper right frame). The diagnostic plot is a straight line so the formula $F_{trans} = -\alpha \, LN(1 - F_{exp}/\alpha)$ has to be applied. From the diagnostic plot the intercepts with the abscissa ($\alpha = 226.8$) and the ordinate ($v_{init} = 8.03$ nM/AU) are obtained. Application to the calibrator line indeed renders a straight line (upper left frame, upper line). The lower left frame shows the fluorescent trace of the thrombin generation experiment (lower curve) and its transformation (upper curve). The lower left frame shows the first derivatives of the direct and transformed data. As $v_{init}$ is obtained with 100 nM (staphylocoagulase-) thrombin, the values on the ordinate have to be multiplied by $100/8.03 = 12.45$ to obtain nM thrombin.

It is seen that in contrast to thrombin generation experiments in bulk fluid (expl 1) but in accordance with the measurement in a thin layer of plasma (expl. 6), the diagnostic plot is a straight line. Like in expl. 6 probably because measurements are made in a thin layer. It is also seen that with this substrate the difference between the correctly calculated thrombin generation and the approximate data that result from direct differentiation of the untransformed curve are small. This illustrates the use of these methods in selecting experimental conditions that do not require complicated data handling.

CITED LITERATURE

1. Hemker H C, Beguin S. Phenotyping the clotting system. *Thromb Haemost* 2000; 84:747-51.
2. Peyrou V, Lormeau J C, Herault J P, Gaich C, Pfliegger A M, Herbert J M. Contribution of erythrocytes to thrombin generation in whole blood. *Thromb Haemost* 1999; 81:400-6.
3. Giesen P L, Rauch U, Bohrmann B, Kling D, Roque M, Fallon J T, Badimon J J, Himber J, Riederer M A, Nemerson Y. Blood-borne tissue factor: another view of thrombosis. *Proc Natl Acad Sci USA* 1999; 96:2311-5.
4. Hemker H C. Platelet procoagulant activities: the amplification loops between platelets and the plasmatic clotting system. In *Platelets, Gresele, Page and Fuster edts.* 2002; Cambridge University Press:381-392.
5. Beguin S, Kumar R. Thrombin, fibrin and platelets: a resonance loop in which von Willebrand factor is a necessary link. *Thromb Haemost* 1997; 78:590-4.
6. Beguin S, Kumar R, Keularts I, Seligsohn U, Coller B S, Hemker H C. Fibrin-dependent platelet procoagulant activity requires GPIb receptors and von willebrand factor [In Process Citation]. *Blood* 1999; 93:564-70.
7. Prevention of pulmonary embolism and deep vein thrombosis with low dose aspirin: Pulmonary Embolism Prevention (PEP) trial. *Lancet* 2000; 355:1295-302.
8. Nicolaes G A, Thomassen M C, Tans G, Rosing J, Hemker H C. Effect of activated protein C on thrombin generation and on the thrombin potential in plasma of normal and APC-resistant individuals. *Blood Coagul Fibrinolysis* 1997; 8:28-38.
9. Rosing J, Tans G, Nicolaes G A, Thomassen M C, van Oerle R, van der Ploeg P M, Heijnen P, Hamulyak K, Hemker H C. Oral contraceptives and venous thrombosis: different sensitivities to activated protein C in women using second- and third-generation oral contraceptives. *Br J Haematol* 1997; 97:233-8.
10. Regnault V, Beguin S, Wahl D, de Maistre E, Coenraad Hemker H, Lecompte T. Thrombinography shows acquired resistance to activated protein C in patients with lupus anticoagulants. *Thromb Haemost* 2003; 89:208-12.
11. Tanis B, Algra A, van der Graaf Y, Helmerhorst F, Rosendaal F. Procoagulant factors and the risk of myocardial infarction in young women. *Eur J Haematol* 2006; 77:67-73.
12. Redondo M, Watzke H H, Stucki B, Sulzer I, Biasiutti F D, Binder B R, Furlan M, Lammle B, Wuillemin W A. Coagulation factors II, V, VII, and X, prothrombin gene 20210G-->A transition, and factor V Leiden in coronary artery disease: high factor V clotting activity is an independent risk factor for myocardial infarction. *Arterioscler Thromb Vasc Biol* 1999; 19:1020-5.
13. Faber C G, Lodder J, Kessels F, Troost J. Thrombin generation in platelet-rich plasma as a tool for the detection of hypercoagulability in young stroke patients. *Pathophysiol Haemost Thromb* 2003; 33:52-8.
14. Dargaud Y, Beguin S, Lienhart A, Al Dieri R, Trzeciak C, Bordet J C, Hemker H C, Negrier C. Evaluation of thrombin generating capacity in plasma from patients with haemophilia A and B. *Thromb Haemost* 2005; 93:475-80.
15. Siegemund T, Petros S, Siegemund A, Scholz U, Engelmann L. Thrombin generation in severe haemophilia A and B: the endogenous thrombin potential in platelet-rich plasma. *Thromb Haemost* 2003; 90:781-6.
16. Keularts I M, Zivelin A, Seligsohn U, Hemker H C, Beguin S. The role of factor XI in thrombin generation induced by low concentrations of tissue factor. *Thromb Haemost* 2001; 85:1060-5.
17. Al Dieri R, Peyvandi F, Santagostino E, Giansily M, Mannucci P M, Schved J F, Beguin S, Hemker H C. The thrombogram in rare inherited coagulation disorders: its relation to clinical bleeding. *Thromb Haemost* 2002; 88:576-82.
18. Keularts I M, Hamulyak K, Hemker H C, Beguin S. The effect of DDAVP infusion on thrombin generation in platelet-rich plasma of von Willebrand type 1 and in mild haemophilia A patients. *Thromb Haemost* 2000; 84:638-42.
19. Dargaud Y, Lienhart A, Meunier S, Hequet O, Chavanne H, Chamouard V, Marin S, Negrier C. Major surgery in a severe haemophilia A patient with high titre inhibitor: use of the thrombin generation test in the therapeutic decision. *Haemophilia* 2005; 11:552-8.
20. Dargaud Y, Bordet J C, Trzeciak M C, Vinciguerra C, Negrier C. A case of Glanzmann's thrombasthenia successfully treated with recombinant factor viia during a surgical procedure: observations on the monitoring and the mechanism of action of this drug. *Haematologica* 2006; 91:ECR20.
21. Hemker H C, Al Dieri R, Beguin S. Thrombin generation assays: accruing clinical relevance. *Curr Opin Hematol* 2004; 11:170-5.
22. Hemker H C, Giesen P, Al Dieri R, Regnault V, De Smedt E, Wagenvoord R, Lecompte T, Beguin S. Calibrated automated thrombin generation measurement in clotting plasma. *Pathophysiol Haemost Thromb* 2003; 33:4-15.
23. Varadi K, Turecek P L, Schwarz H P. Thrombin generation assay and other universal tests for monitoring haemophilia therapy. *Haemophilia* 2004; 10 Suppl 2:17-21.
24. Hemker H C, Giesen P L, Ramjee M, Wagenvoord R, Beguin S. The thrombogram: monitoring thrombin generation in platelet-rich plasma. *Thromb Haemost* 2000; 83:589-91.
25. Hemker H C, Beguin S. Thrombin generation in plasma: its assessment via the endogenous thrombin potential. *Thromb Haemost* 1995; 74:134-8.
26. Meyer H D, Keller H. One-point recalibration of heterogeneous enzyme immunoassays with non-linear calibration curves. *Clin Chem* 1988; 34:113-7.

27. Heller J H, Setlow R B, Mylon E. Fluorimetric studies on epinephrine and l-arterenol in plasma. *Am J Physiol* 1951; 166:304-13.
28. Silva L C, Trevisan M G, Poppi R J, Sena M M. Direct determination of propranolol in urine by spectrofluorimetry with the aid of second order advantage. *Anal Chim Acta* 2007; 595:282-8.
29. Palmier M O, Van Doren S R. Rapid determination of enzyme kinetics from fluorescence: overcoming the inner filter effect. *Anal Biochem* 2007; 371:43-51.
30. Goudar C T, Harris S K, McInerney M J, Suflita J M. Progress curve analysis for enzyme and microbial kinetic reactions using explicit solutions based on the Lambert W function. *J Microbiol Methods* 2004; 59:317-26.
31. Holzhutter H G, Henke W. A new method of parameter estimation from progress curves. *Biomed Biochim Acta* 1984; 43:813-20.
32. Kuttner G A, Holzhutter H G, Frommel C. The use of progress curves for the estimation of inactivation rate constants of enzymes. *Biomed Biochim Acta* 1985; 44:1025-34.
33. Hemker H C, de Smedt E. Caution in the interpretation of continuous thrombin generation assays. A rebuttal. *J Thromb Haemost* 2007; 5:1085-7.
34. Hemker H C, Wielders S, Kessels H, Beguin S. Continuous registration of thrombin generation in plasma, its use for the determination of the thrombin potential. *Thromb Haemost* 1993; 70:617-24.
35. Ramjee M K. The use of fluorogenic substrates to monitor thrombin generation for the analysis of plasma and whole blood coagulation. *Anal Biochem* 2000; 277:11-8.
36. Hendrix H, Lindhout T, Mertens K, Engels W, Hemker H C. Activation of human prothrombin by stoichiometric levels of staphylocoagulase. *J Biol Chem* 1983; 258:3637-44.

The invention claimed is:

1. A method of determining amidolytic enzyme activity in a sample over a given period of time based on conversion of a fluorogenic or chromogenic substrate of the enzyme, comprising the steps of:
measuring a signal ($F_{diag}$) produced from splitting said substrate by enzymatic activity after contact with a determined initially fixed concentration of the enzyme (E) over a time period (t) so as to correctly obtain calibration under initial conditions, and preparing a diagnostic time curve from $F_{diag}$ measured over time;
preparing a diagnostic plot from a first derivative of said diagnostic time curve against $F_{diag}$, said diagnostic plot being a straight line or a parabolic line at least over a portion of said diagnostic plot, wherein the initial rate of substrate conversion ($v_{init}$) is where the diagnostic plot intercepts the ordinate and the theoretical upper limit of the signal ($\alpha$) is where the diagnostic plot intercepts the abscissa, said diagnostic plot providing calibration under initial conditions;
measuring an experimental signal produced by the sample ($F_{exp}$) resulting from splitting the substrate by enzymatic activity from the enzyme, said enzyme activity generating in and/or disappearing from the sample over a period of time, the $F_{exp}$ and $F_{diag}$ being measured under identical conditions;
preparing an experimental time curve $F_{exp}=f(t)$ from the $F_{exp}$ measured over time;
transforming the $F_{exp}$ into an ideal value ($F_{transf}$) by an equation according to:
(i) $F_{transf}=-(\alpha \ln(1-F_{exp}/\alpha)$ for a portion of the diagnostic plot that forms a straight line;
(ii) $F_{transf}=\alpha \arctan h(F_{exp}/\alpha)$ for a portion of the diagnostic plot that forms a parabolic line; and
determining the enzyme concentration ($E_{exp}$) from $E_{exp}=v_{init}F_{transf}/dt$ so that the enzymatic activity over a given period of time is determined without continuous comparison to an array of values or a calibrator curve simultaneously obtained from a parallel calibration experiment.

2. The method of claim 1, wherein $\alpha$ is determined either by trial and error so as to render constant the increase of measured signal over that part of a $F_{exp}=f(t)$ curve where the enzymatic activity is known to be constant, or by fitting to that part of the experimental curve the appropriate mathematical function, which is a curve according to $F=\alpha \tan h(bt)$ when the diagnostic plot is a parabola or a curve according to $F=\alpha(1-\exp(-bt))$ when the diagnostic plot is rectilinear.

3. The method of claim 2, wherein the sample is a blood sample or a plasma sample.

4. The method of claim 1, wherein the $F_{exp}$ is measured from the enzyme activity generating in the sample over the period of time.

5. The method of claim 1, wherein the $F_{exp}$ is measured from the enzyme activity disappearing from the sample over the period of time.

6. The method of claim 1, wherein the enzyme activity is determined with a chromogenic substrate.

7. The method of claim 1 wherein the enzymatic activity of thrombin in a plasma or in a blood sample is determined and wherein the substrate for thrombin is a chromogenic substrate.

8. The method of claim 1 wherein the enzymatic activity of thrombin in a plasma or in a blood sample is determined and wherein the substrate for thrombin is a fluorogenic substrate.

9. The method of claim 1 wherein the enzymatic activity of plasmin in a plasma or in a blood sample is determined and wherein the substrate for plasmin is a chromogenic substrate.

10. The method of claim 1 for the determination of the enzymatic activity of plasmin in a plasma or in a blood sample, wherein the substrate for plasmin is a fluorogenic substrate.

11. The method of claim 10, wherein the fluorogenic substrate is a synthetic substrate for thrombin, coupled with a fluorescent molecule.

12. The method according to claim 11, wherein the thrombin substrate is selectively hydrolyzed by thrombin, has a moderate binding affinity for thrombin and a low kinetic constant.

13. The method according to claim 11, wherein the fluorogenic substrate is an oligopeptide having a sequence of 2 to 30 amino acid residues coupled with a fluorescent molecule.

14. The method according to claim 13, wherein the oligopeptide has a terminal lysine or arginine for coupling with a fluorescent molecule.

15. The method of claim 8, wherein the fluorogenic substrate is Z-Gly-Gly-Arg-AMC, BZ-Phe-Val-Arg-AMC, Z-Pro-Arg-AMC or Z-Gly-Pro-Arg-AMC.

16. The method of claim 6, wherein the chromogenic substrate is MSCValArg-pMA.

17. The method according to claim 1, wherein, for the preparation of the diagnostic plot, the substrate is present at time zero at a concentration within a range of up to three times the Km of the enzyme.

18. The method of claim 6, wherein the chromogenic substrate is H-D-Phe-Pip-Arg-pNA, Msc-Val-Arg-pNA, MZ-Aib-Arg-pNA or DEMZ-Gly-Arg-pNA.

19. The method of claim 1 wherein, for the preparation of the diagnostic plot, the initial concentration of the enzyme is within a range of 10 nm to 1 μM and the substrate is present at time zero at a concentration within a range of 0.01-3 times the Km value of the enzyme.

20. The method according to claim 1, wherein the enzymatic activity over a period of time is used for detecting or monitoring a haemostatic disease or a thrombotic disease.

21. The method according to claim 1, wherein the enzymatic activity over a period of time is used for detecting or monitoring interactions of determined substance(s) on thrombin activity in a whole blood sample, wherein said determined substance(s) is (are) added to the sample or is (are) added during thrombin generation.

22. The method according to claim 21, wherein the enzymatic activity over a period of time is used for monitoring interaction of coagulation factors or drugs.

23. The method according to claim 21, wherein the enzymatic activity over a period of time is used for screening substances to determine their interacting capacity with thrombin generation.

24. The method according to claim 1, wherein the enzymatic activity over a period of time is used for measurement of Endogenous Thrombin Potential (ETP) of the whole blood sample.

25. The method according to claim 1, wherein the enzymatic activity over a period of time is used for measurement of time to peak of thrombin.

26. The method according to claim 1, wherein the enzymatic activity over a period of time is used for measurement of clotting time.

27. The method according to claim 1, wherein the enzymatic activity over a period of time is used for measurement of the level of the peak of thrombin generated.

28. The method of claim 6, wherein the enzyme activity is determined with a chromogenic substrate and measuring the $F_{diag}$ and the $F_{exp}$ comprises measuring the optical density of the substrate.

* * * * *

UNITED STATES PATENT AND TRADEMARK OFFICE
CERTIFICATE OF CORRECTION

PATENT NO. : 8,551,722 B2  Page 1 of 1
APPLICATION NO. : 12/866777
DATED : October 8, 2013
INVENTOR(S) : LM Hemker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Fifteenth Day of September, 2015

Michelle K. Lee
*Director of the United States Patent and Trademark Office*